(12) United States Patent
Constantine et al.

(10) Patent No.: US 11,854,701 B2
(45) Date of Patent: Dec. 26, 2023

(54) TIME WINDOW-BASED PLATFORM FOR THE RAPID STRATIFICATION OF BLUNT TRAUMA PATIENTS INTO DISTINCT OUTCOME COHORTS

(71) Applicant: University of Pittsburgh—Of the Commonwealth System of Higher Education, Pittsburgh, PA (US)

(72) Inventors: Gregory M. Constantine, Baden, PA (US); Timothy Billiar, Presto, PA (US); Qi Mi, Pittsburgh, PA (US); Rami Namas, Bethel Park, PA (US); Lukas Schimunek, Rimbach (DE); Yoram Vodovotz, Sewickley, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/473,726

(22) Filed: Sep. 13, 2021

(65) Prior Publication Data
US 2022/0215963 A1 Jul. 7, 2022

Related U.S. Application Data

(63) Continuation of application No. 15/971,519, filed on May 4, 2018, now abandoned.
(Continued)

(51) Int. Cl.
*G16H 50/30* (2018.01)
*G16H 20/10* (2018.01)
*G16H 50/20* (2018.01)
*G16H 50/70* (2018.01)
*G16B 20/20* (2019.01)
*G16B 40/00* (2019.01)
*G16B 40/30* (2019.01)
*G16H 70/40* (2018.01)

(52) U.S. Cl.
CPC ............ *G16H 50/30* (2018.01); *G16B 20/20* (2019.02); *G16B 40/00* (2019.02); *G16B 40/30* (2019.02); *G16H 20/10* (2018.01); *G16H 50/20* (2018.01); *G16H 50/70* (2018.01); *G16H 70/40* (2018.01)

(58) Field of Classification Search
CPC .................. G16H 50/30; G06Q 50/22–24
See application file for complete search history.

(56) References Cited

U.S. PATENT DOCUMENTS 9,417,250 B2 8/2016 Anderberg et al.
9,420,957 B2 8/2016 Ong et al.
(Continued)

OTHER PUBLICATIONS

Multiple organ dysfunction syndrome (MODS) prediction score in multi-trauma patients; Rendy et al.; Published May 1, 2017 (Year: 2017).*
(Continued)

*Primary Examiner* — John A Pauls
(74) *Attorney, Agent, or Firm* — The Webb Law Firm

(57) ABSTRACT

Provided herein are methods for segregating trauma, e.g., blunt trauma, patients into different cohorts based on risk of multiple organ dysfunction syndrome using patient data obtained within a short time window following injury. The methods are useful in providing treatment to trauma patients, and for separating trauma patients into cohorts.

20 Claims, 10 Drawing Sheets
Specification includes a Sequence Listing.

Related U.S. Application Data

(60) Provisional application No. 62/502,018, filed on May 5, 2017.

(56) References Cited

U.S. PATENT DOCUMENTS

| | | | |
|---|---|---|---|
| 9,423,372 | B2 | 8/2016 | Bar-Or et al. |
| 9,470,695 | B2 | 10/2016 | Anderberg et al. |
| 9,551,720 | B2 | 1/2017 | Singbartl et al. |
| 2010/0136562 | A1* | 6/2010 | Shimada .............. C12Q 1/6883 435/6.16 |
| 2012/0156230 | A1* | 6/2012 | Abbot ...................... A61P 3/02 424/184.1 |

OTHER PUBLICATIONS

Citation for Rendy et al.: (Year: 2017).*
"Which score should be used for posttraumatic multiple organ failure?—Comparison of the MODS, Denver and SOFA Scores"; Frohlich et al.; Nov. 3, 2016 (Year: 2016).*
"The Wilcoxon Rank-Sum Test"; Wild; 1997 (Year: 1997).*
Delong et al., Cytokines in Patients with Polytrauma,n Clinical Orthopaedics and Related Research, 2004, pp. 67-65, No. 422.
Fann et al., "The Use of Prognostic Indicators in the Development of a Statistical Model Predictive for Adrenal Insufficiency in Trauma Patients," Department of Surgery, University of South Carolina, 2007, pp. 210-214, vol. 73, No. 3.
Giannoudis et al., "Immediate IL-10 expression following major orthopaedic trauma: relationship to anti-inflammatory) response and subsequent development of sepsis," Intensive Care Medicine, 2000, pp. 1076-1081, vol. 26.
Giannoudis et al., "The genetic predisposition to adverse outcome after trauma," J Bone Joint Surg [Br.], 2007, pp. 1273-1279, vol. 89-B, No. 10.
Gouel-Cheron et al., Early Interleukin-6 and Slope of Monocyte Human Leukocyte Antigen-DR: A Powerful Association to Predict the Development of Sepsis after Major Trauma: PLoS One, 2012, pp. 1-9, vol. 7, Issue 3.
Gu et al., "Clinical relevance of 13 cytokine gene polymorphisms in Chinese major trauma patients," Intensive Care Med, 2010, pp. 1261-1265, vol. 36.
Hannan et al., "Predictors of Mortality in Adult Patients with Blunt Injuries in New York State: A Comparison of the Trauma and Injury Severity Score (TRISS) and the International Classification of Disease, Ninth Revision-based Injury Severity Score (ICISS)," Journal of Trauma and Acute Care Surgery, 1999, pp. 8-14, vol. 47, Issue 1.
Hildebrand et al., "Association of IL-8-251AfT polymorphism with incidence of Acute Respiratory Distress Syndrome (ARDS) and IL-8 synthesis after multiple trauma," Cytokine, 2007, pp. 192-199, vol. 37.
Hildebrand et al., "Genetic predisposition for a compromised immune system after multiple trauma," Shock, 2005, pp. 518-522, vol. 24, Issue 6.
Ho et al., "A mathematical model for fresh frozen plasma transfusion strategies during major trauma resuscitation with ongoing hemorrhage," J can chir, 2005, pp. 470-478, vol. 48, No. 6.
Horan et al., "CDC/NHSN surveillance definition of health care-associated infection and criteria for specific types of Infections in the acute care setting," Am J Infect Control, 2008, pp. 309-332, vol. 36.
Hranjec et al., "Mortality Factors in Geriatric Blunt Trauma Patients: Creation of a Highly Predictive Statistical Model for Mortality Using 50,765 Consecutive Elderly Trauma Admissions from the National Sample Project," Am Surg., 2012, pp. 1369-1375, vol. 78, No. 12.
https://www-01.ibm.com/support/docview.wss?uid=swg27043831, IBM SPSS Modeler 17 Algorithms Guide.
Jawa et al., "Interleukin-6 in Surgery, Trauma, and Critical Care Part II: Clinical Implications," Journal of Intensive Care Medicine, 2011, pp. 73-87, vol. 26, No. 2.
Jiang et al., "Kinetics of plasma cytokines and its clinical significance in patients with severe trauma," Chinese Medical Journal (English), 1997, pp. 923-926, vol. 110, No. 12.
Kashiwabara et al., "Surgical trauma-induced adrenal insufficiency is associated with postoperative inflammatory responses," J Nippon Med Sch, 2007, pp. 274-283, vol. 74, No. 4.
Kauvar et al., "Impact of Hemorrhage on Trauma Outcome: An Overview of Epidemiology, Clinical Presentations, and Therapeutic Considerations," The Journal of Trauma Injury, Infection, and Critical Care, 2006, pp. S3-S11, vol. 60, No. 6.
Kroezen et al., "Base Deficit-Based Predictive Modeling of Outcome in Trauma Patients Admitted to Intensive Care Units in Dutch Trauma Centers," The Journal of Trauma Injury, Infection, and Critical Care, 2007, pp. 908-913, vol. 63.
Kuhls et al., "Predictors of mortality in adult trauma patients: the Physiologic Trauma Score is equivalent to the Trauma and Injury Severity Score," Journal of the American College of Surgeons, 2002, pp. 695-704, vol. 194.
Laun et al., "Transforming growth factor-beta1 and major trauma: time-dependent association with hepatic and renal Insufficiency," Shock, 2003, pp. 16-23, vol. 29, No. 1.
Lenz et al., "Systemic inflammation after trauma," Injury, Int. J. Care Injured, 2007, pp. 1336-1345, vol. 38.
Maier et al., "Early versus late onset of multiple organ failure is associated with differing patterns of plasma cytokine biomarker expression and outcome after severe trauma," Shock, 2007, pp. 668-674, vol. 28, No. 6.
Majetschak et al., "Systemic Ubiquitin Release After Blunt Trauma and Burns: Association With Injury Severity, Posttraumatic Complications, and Survival," The Journal of Trauma Injury, Infection, and Critical Care, 2008, pp. 586-598, vol. 64.
Majetschak et al., "Tumor necrosis factor gene polymorphisms, leukocyte function, and sepsis susceptibility in blunt trauma patients," Clinical and Diagnostic Laboratory Immunology, 2002, pp. 1205-1211, vol. 9, No. 6.
Marshall et al., "Multiple Organ Dysfunction Score: A reliable descriptor of a complex clinical outcome", Critical Care Medicine, 1995, pp. 1638-1652, vol. 23, No. 10.
Marshall et al., "What is an intensive care unit? A report of the task force of the World Federation of Societies of Intensive and Critical Care Medicine," Journal of Critical Care, 2017, pp. 270-276, vol. 37.
Martin et al., "Patterns of cytokine evolution (tumor necrosis factor-alpha and interleukin-6) after septic shock, hemorrhagic shock, and severe trauma" Critical Care Medicine 1997, pp. 1813-1819, vol. 25, No. 11.
May et al., "Estradiol is associated with mortality in critically ill trauma and surgical patients," Grit Care Med., 2008, pp. 62-68, vol. 36, No. 1.
McDaniel et al., "Molecular Analysis of Inflammatory Markers in Trauma Patients at Risk of Postinjury Complications," Journal of Trauma and Acute Care Surgery, 2007, pp. 147-158, vol. 63, Issue 1.
Meert et al., "Altered T Gel Cytokine Production Following Mechanical Trauma," Annals of Clinical and Laboratory Science, 1996, pp. 283-288, vol. 28, No. 5.
Menges et al., "Sepsis syndrome and death in trauma patients are associated with variation in the gene encoding tumor necrosis factor," Critical Care Medicine, 2008, pp. 1-19, vol. 36, Issue 5.
Mitra et al., "Predicting massive blood transfusion using clinical scores post-trauma," VoxSanguinis, 2012, pp. 324-330, vol. 102.
Mokart et al., "Early postoperative compensatory anti-inflammatory response syndrome is associated with septic complications after major surgical trauma in patients with cancer," British Journal of Surgery, 2002, pp. 1450-1456, vol. 89.
Mommsen et al., "Elevated systemic IL-18 and neopterin levels are associated with posttraumatic complications among patients with multiple injuries: A prospective cohort study," Injury, 2009, pp. 528-534, vol. 40.

(56) References Cited

OTHER PUBLICATIONS

Morris et al., "Adrenal Insufficiency, Heart Rate Variability, and Complex Biologic Systems: A Study of 1,871 Critically III Trauma Patients," Journal of the American College of Surgeons, 2007, pp. 885-893, vol. 204.

Namas et al., "An Adequately Robust Early TNF-a Response Is a Hallmark of Survival Following Trauma/ Hemorrhage," PLoS One, 2009, pp. 1-13, vol. 4, Issue 12.

Namas et al., "Individual-Specific Principal Component Analysis of Circulating Inflammatory Mediators Predicts Early Organ Dysfunction in Trauma Patients," J Crit Care., 2016, pp. 146-153, vol. 36.

Napolitano et al., "Immune Dysfunction in Trauma," Surgical Clinics of North America, 1999, pp. 1385-1416, vol. 179, No. 6.

Nast-Kolb et al., "Indicators of the Posttraumatic Inflammatory Response Correlate with Organ Failure in Patients With Multiple Injuries," The Journal of Trauma: Injury, Infection, and Critical Care, 1997, pp. 446-455, vol. 42, No. 3.

The Systemic Inflammatory Response; Barton et al.; 2012 (Year: 2012).

O'Keefe et al., "An evaluation of risk factors for mortality after burn trauma and the identification of gender-dependent differences in outcomes," Journal of the American College of Surgeons, 2001, pp. 153-160, vol. 192.

D'Keefe et al., "The G->A single nucleotide polymorphism at the -308 position in the tumor necrosis factor-a promoter increases the risk for severe sepsis after trauma," Journal of Trauma and Acute Care Surgery, 2002, pp. 617-826, vol. 52, Issue 5.

Partrick et al., "Release of anti-inflammatory mediators after major torso trauma correlates with the development of postinjury multiple organ failure," The American Journal of Surgery, 1999, pp. 564-569, vol. 178.

Pedregosa et al., "Scikit-learn: Machine Learning in Python," Journal of Machine Learning Research, 2011, pp. 2825-2830, vol. 12.

Peltz et al., "HMGB1 is markedly elevated within 6 hours of mechanical trauma in humans," Shock, 2009, pp. 17-22, vol. 32, No. 1.

Puyana et al., "Both T-Helper-1- and T-Helper-2-Type Lymphokines Are Depressed in Posttrauma Anergy," The Journal of Trauma: Injury, Infection, and Critical Care, 1998, pp. 1037-1046, vol. 44, No. 6.

Rajicic et al., "Identification and Interpretation of Longitudinal Gene Expression Changes in Trauma," PLoS One, 2010, pp. 1-8, vol. 5, Issue 12.

Riordan et al., "Early Loss of Heart Rate Complexity Predicts Mortality Regardless of Mechanism, Anatomic ocation, or Severity of Injury in 2178 Trauma Patients," Journal of Surgical Research, 2009, pp. 283-289, vol. 156.

Rixen et al., "Physiologic state severity classification as an indicator of posttrauma cytokine response," Shock, 1995, pp. 27-38, vol. 4, No. 1.

Rixen et al., "Plasma nitric oxide in posttrauma critical illness: a function of "sepsis" and the physiologic state severity classficiation quantifying the probability of death," Shock, 1997, pp. 17-28, vol. 7, No. 1.

Rixen et al., "[Predicting the outcome in severe injuries: an analysis of 2069 patients from the trauma register of the German Society of Traumatology (DGU)]," Unfallchirurg, 2001, pp. 230-239, vol. 104, No. 3.

Rixen et al., ""Sepsis/SIRS," Physiologic Classification, Severity Stratification, Relation to Cytokine Elaboration and Outcome Prediction in Posttrauma Critical Illness," The Journal of Trauma: Injury, Infection, and Critical Care, 1996, pp. 581-598, vol. 41, No. 4.

Rose et al., "Mediators in polytrauma—pathophysiological significance and clinical relevance," Langenbeck's Archives of Surgery, 1998, pp. 199-208, vol. 383.

Roumen et al., "Cytokine Patterns in Patients After Major Vascular Surgery, Hemorrhagic Shock, and Severe Blunt Trauma: Relation with Subsequent Adult Respiratory Distress Syndrome and Multiple Organ Failure," Annals of Surgery, 1993, pp. 769-776, vol. 218, No. 6.

Schimunek et al., "An Enrichment Strategy Yields Seven Novel Single Nucleotide Polymorphisms Associated With Mortality and Altered Th17 Responses Following Blunt Trauma," Shock, 2018, pp. 259-268, vol. 49, No. 3.

Schinkel et al., "Analysis of Systemic Interleukin-11 After Major Trauma," Shock, 2005, pp. 30-34, vol. 23, No. 1.

Schinkel et al., "Kinetics of circulating adhesion molecules and chemokines after mechanical trauma and burns," Eur J Surg, 1996, pp. 763-768, vol. 162.

Schluter et al., "Using Trauma Injury Severity Score (TRISS) variables to predict length of hospital stay following Trauma in New Zealand," The New Zealand Medical Journal, 2009, pp. 1-14, vol. 122, No. 1302.

Schroeder et al., "The—1082 interleukin-10 polymorphism is associated with acute respiratory failure after major Trauma: A prospective cohort study," Surgery, 2008, pp. 233-242, vol. 143.

Seekamp et al., "Cytokines and Adhesion Molecules in Elective and Accidental Trauma-Related Ischemia/ Reperfusion," The Journal of Trauma: Injury, Infection, and Critical Care, 1998, pp. 874-882, vol. 44, No. 5.

Shepherd et al., "Contemporary Patterns of Multiple Organ Dysfunction in Trauma," Shock, 2017, pp. 429-435, vol. 47, No. 4.

Shoemaker, "New approaches to trauma management using severity of illness and outcome prediction based on honinvasive hemodynamic monitoring," Surgical Clinics of North America, 2002, pp. 245-255, vol. 82, No. 1.

Sousa et al., "Measurement of cytokines and adhesion molecules in the first 72 hours after severe trauma: association with severity and outcome," Disease Markers, 2015, pp. 1-8, vol. 2015.

Spielmann et al., "Early detection of increased tumour necrosis factor alpha {TNFa) and soluble TNF receptor protein plasma levels after trauma reveals associations with the clinical course," Acta Anaesthesiol Scand., 2001, pp. 364-370, vol. 45.

Spolarics et al., "Depressed interleukin-12-producing activity by monocytes correlates with adverse clinical course and a shift toward Th2-type lymphocyte pattern in severely injured male trauma patients," Critical Care Medicine, 2003 pp. 1722-1729, vol. 31, Issue 6.

Surbatovic et al., "Immune Cytokine Response in Combat Casualties: Blast or Explosive Trauma with or without Secondary Sepsis," Military Medicine, 2007, pp. 190-195, vol. 172, No. 2.

Svoboda et al., "Dynamics of Interleukin 1, 2, and 6 and Tumor Necrosis Factor Alpha in Multiple Trauma Patients," The Journal of Trauma, 1994, pp. 336-340, vol. 36, No. 3.

Swanson et al., "Developing a Gene Expression Model for Predicting Ventilator-Associated Pneumonia in Trauma Patients: A Pilot Study," PLoS One, 2012, pp. 1-7, vol. 7, Issue 8.

Vogel et al., "Prediction of postinjury multiple-organ failure in the emergency department: Development of the Denver Emergency Department Trauma Organ Failure Score," J. Trauma Acute Care Surg., 2014, pp. 140-145, vol. 76, No. 1.

Warren et al., "A genomic score prognostic of outcome in trauma patients," Mol Med., 2009, 220-227, vol. 15, Nos. 7-8.

Wichmann et al., "Severe depression of host immune functions following closed-bone fracture, soft-tissue trauma, and hemorrhagic shock," Critical Care Medicine, 1998, pp. 1372-1378, vol. 26, No. 8.

Zaaqoq et al., "IP-10, a potential driver of neurally-controlled interleukin-10 and morbidity in human blunt trauma," Crit Care Med., 2014, pp. 1487-1497, vol. 42, No. 6.

Ziraldo et al., "Central Role for MCP-1/CCL2 in Injury-Induced Inflammation Revealed by In Vitro, In Silica, and Clinical Studies," PLoS One, 2013, pp. 1-18, vol. 8, Issue 12.

Balendran et al., Prothrombin time is predictive of low plasma prothrombin concentration and clinical outcome in patients with trauma hemorrhage: analyses of prospective observational cohort studies, Scandinavian Journal of Trauma, Resuscitation and Emergency Medicine, 2017, pp. 1-10, vol. 25, No. 30.

(56) References Cited

OTHER PUBLICATIONS

Batchinsky et al., "Rapid Prediction of Trauma Patient Survival By Analysis of Heart Rate Complexity: Impact of Reducing Data Set Size," Shock, 2009, pp. 565-571, vol. 32, No. 6.

Breiman, "Random Forests", Machine Learning, 2001, pp. 5-32, vol. 45.

Brown et al., "Trauma in silico: Individual-specific mathematical models and virtual clinical populations," Science Translational Medicine, 2015, pp. 1-11, vol. 7, Issue 285.

Cancio et al., "Heart-Rate Complexity for Prediction of Prehospital Lifesaving Interventions in Trauma Patients," The Journal of Trauma Injury, Infection, and Critical Care, 2008, pp. 813-819, vol. 65, No. 4.

Cannon, "A Mathematical Model of Hemorrhagic Shock: The Future of Trauma Triage," Military Medicine, 2002, pp. 312-316, vol. 167, No. 4.

Catania, "Immunological Consequences of Trauma and Schock," Ann Acad Med Singapore, 1999, pp. 120-132, vol. B.

Chawda et al., "Predicting outcome after multiple trauma: which scoring system?" Injury, Int. J. Care Injured, 2004, pp. 347-358, vol. 35.

Cohen et al., "Early release of high mobility group box nuclear protein 1 after severe trauma in humans: role of injury severity and tissue hypoperfusion," Critical Care, 2009, pp. 1-10, vol. 13.

Cohen et al., "Identification of complex metabolic states in critically injured patients using bioinformatic cluster Analysis," Critical Care, 2010, pp. 1-11, vol. 14.

Constantine et al., "Dynamic Profiling: Modeling the Dynamics of Inflammation and Predicting Outcomes in Traumatic Brain Injury Patients," Frontiers in Pharmacology, 2016, pp. 1-9, vol. 7.

Delong et al., "Cytokines in Patients with Polytrauma," Clinical Orthopaedics and Related Research, 2004, pp. 57-65, No. 422.

\* cited by examiner

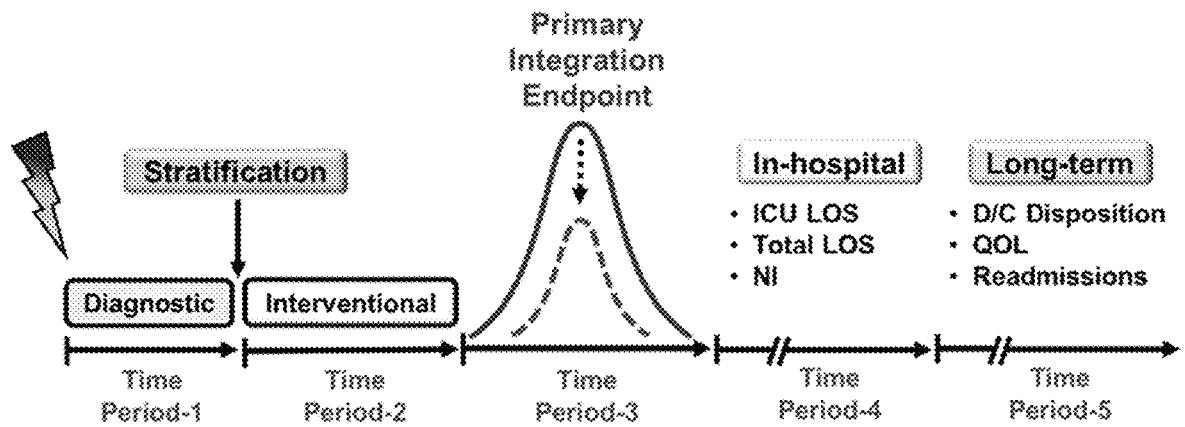

Fig. 2

| | Nosocomial Infection | AUC of the receiver operating characteristic | Std. Error | Significance | Asymptomatic 95% Confidence interval | |
|---|---|---|---|---|---|---|
| | | | | | Lower bound | Upper bound |
| 1 | $aMOD_{3,5}$ | 0.738 | 0.028 | 0.0001 | 0.682 | 0.793 |
| 2 | $aMOD_{2,5}$ | 0.734 | 0.028 | 0.0001 | 0.678 | 0.789 |
| 3 | $aMOD_{3,4}$ | 0.732 | 0.028 | 0.0001 | 0.677 | 0.787 |
| 4 | $MOD_3$ | 0.731 | 0.028 | 0.0001 | 0.676 | 0.786 |
| 5 | $aMOD_{2,4}$ | 0.729 | 0.028 | 0.0001 | 0.673 | 0.784 |

| | ICU length of stay | Spearman correlation coefficient | $P$ value |
|---|---|---|---|
| 1 | $aMOD_{2,5}$ | 0.656 | <0.001 |
| 2 | $aMOD_{2,4}$ | 0.650 | <0.001 |
| 3 | $aMOD_{3,5}$ | 0.646 | <0.001 |
| 4 | $aMOD_{3,4}$ | 0.644 | <0.001 |
| 5 | $mMOD_{3,5}$ | 0.641 | <0.001 |

| | Hospital length of stay | Spearman correlation coefficient | $P$ value |
|---|---|---|---|
| 1 | $aMOD_{2,5}$ | 0.619 | <0.001 |
| 2 | $aMOD_{2,4}$ | 0.609 | <0.001 |
| 3 | $mMOD_{2,5}$ | 0.605 | <0.001 |
| 4 | $aMOD_{3,5}$ | 0.604 | <0.001 |
| 5 | $aMOD_{3,4}$ | 0.598 | <0.001 |

Fig. 3

| Decision list analysis based on nosocomial infection outcome | Cover (n) | Frequency | Percentage of NI |
|---|---|---|---|
| $aMOD_{3-5} > 3.000$ | 72 | 44 | 61.11 % |
| $aMOD_{4-5} > 2.500$ | 71 | 44 | 61.97 % |
| $aMOD_{2-4} > 3.333$ | 69 | 43 | 62.32 % |
| $aMOD_{3-5} > 3.000$ | 71 | 43 | 60.56 % |
| $aMOD_{2-3} > 3.500$ | 71 | 43 | 60.56 % |
| $aMOD_{3-4} > 3.000$ | 75 | 44 | 58.67 % |

*Fig. 4*

|  | aMOD$_{2-5}$ ≤ 3 n=304 | aMOD$_{2-5}$ > 3 n=72 | P value |
|---|---|---|---|
| Biochemical | | | |
| Base deficit (BD) | 5.1 ± 0.3 (n=193) | 6.5 ± 0.5 (n=70) | 0.002 |
| Lactate | 2.7 ± 0.1 (n=211) | 3.4 ± 0.2 (n=70) | 0.004 |
| Sodium (Na) | 138.1 ± 0.2 | 139 ± 0.4 | 0.041 |
| Potassium (K) | 3.9 ± 0.03 | 3.9 ± 0.09 | 0.4 |
| Chloride (Cl) | 106.1 ± 0.3 | 107.7 ± 0.6 | 0.035 |
| Carbon dioxide ($CO_2$) | 23.1 ± 0.2 | 21.8 ± 0.4 | 0.009 |
| Anion gap | 9.9 ± 0.2 | 9.9 ± 0.5 | 0.7 |
| Blood urea nitrogen (BUN) | 14.8 ± 0.4 | 15.3 ± 1.1 | 0.7 |
| Creatinine | 1.03 ± 0.03 | 1.32 ± 0.09 | <0.001 |
| Glucose | 154 ± 3.5 | 168.6 ± 7.1 | 0.044 |
| White blood cell count | 15.6 ± 0.4 | 16.3 ± 0.9 | 0.5 |
| Hemoglobin | 12.9 ± 0.1 | 12.5 ± 0.3 | 0.14 |
| Platelets | 236.8 ± 4.3 | 214.5 ± 9.1 | 0.03 |
| Hematocrit | 37.9 ± 0.3 | 36.5 ± 0.8 | 0.06 |
| Neutrophils | 75.3 ± 0.7 | 73 ± 1.5 | 0.16 |
| Lymphocytes | 15.3 ± 0.5 | 17.1 ± 1.3 | 0.25 |
| Monocytes | 5.8 ± 0.1 | 5.1 ± 0.3 | 0.009 |
| Eosinophils | 0.9 ± 0.06 | 0.8 ± 0.1 | 0.2 |
| Basophils | 0.18 ± 0.02 | 0.17 ± 0.04 | 0.7 |
| Physiological | | | |
| Heart rate | 94.6 ± 1.3 | 99.3 ± 2.9 | 0.16 |
| Blood pressure | 124.7 ± 1.7 | 114.9 ± 3.9 | 0.01 |
| Shock Index (SI) | 0.86 ± 0.04 | 0.99 ± 0.08 | 0.008 |
| Coagulation status | | | |
| International normalized ratio (INR) | 1.2 ± 0.01 | 1.4 ± 0.06 | <0.001 |
| Prothrombin time (PT), seconds | 14.6 ± 0.15 | 16.1 ± 0.6 | 0.001 |
| Partial thromboplastin time (PTT), seconds | 26.6 ± 0.2 | 28.8 ± 0.9 | 0.002 |

*Fig. 5*

| Reference SNP | Position | Base variation | Gene name | Chromosome | Sequence |
|---|---|---|---|---|---|
| AA | | | | | |
| rs10741668 | 15277363 | [T/C] | ? | Chr 11, p14.1 | CAGCGTTTTACAGATGAAGAATCCAA[A/G]GTACACAGATGTCAAAGGGCTTGG |
| rs10790334 | 98885933 | [A/G] | ? | Chr 11, q14 | GTAAAATTCAAACTTTGTCTGTA[C/T]GTGTATGATTTCCAAGCTATTCTA |
| rs2065418 | 30406521 | [A/C] | MPPED2 | Chr 11, p14.1 | GGCTAATATTAACACTGACATCTGC[A/C]AAGTAATATTGGAATGGACATCCAA |
| AB | | | | | |
| rs2241777 | 103400160 | [T/G] | SLC25A32 | Chr 8, q22.3 | AACGTAGAAATCTGTGAAACTCTAT[A/C]CTTCGTCGTCAGTTTTAACATTGTGT |
| rs3134287 | 103411258 | [T/C] | SLC25A32 | Chr 8, q22.3 | CCCACCTTAGTTAGATACGTTACTC[C/T]TTATCCTCCTGCTCCATTTCCCAA |
| rs3098223 | 103434677 | [A/G] | DCAF13 | Chr 8, q22.3 | TACTGGTGATATGTAAGAGTGAACA[C/T]GGCGTTCAAAGGGTGAATCAAAAT |
| rs906790 | 76161264 | [A/G] | ? | Chr 13, q21 | CTTCACTCAGTCAAAAAATTCATG[C/T]TAAGCCAGCCAGGTTTACACACATT |

Fig. 8

|  | rs2065418 AA high ISS n= 35 | Control high ISS n= 49 | p-value |
|---|---|---|---|
| Age (years) | 42.5 ± 3.1 | 41 ± 2.6 | 0.71 |
| ISS | 36 ± 1.5 | 33.5 ± 0.9 | 0.33 |
| Gender | Female: 12<br>Male: 23 | Female: 11<br>Male: 38 | 0.33 |

*Fig. 10*

| | Inflammatory Mediators | p-value |
|---|---|---|
| elevated | Eotaxin | 0.001 |
| | MCP-1 | 0.0001 |
| | MIG | 0.04 |
| lowered | GM-CSF | 0.04 |
| | IFN-α | 0.006 |
| | IL-4 | 0.04 |
| | IL-9 | 0.006 |
| | IL-10 | <0.0001 |
| | IL-15 | 0.02 |
| | IL-17A | 0.002 |
| | IL-23 | 0.03 |

```
                            SEQUENCE LISTING

<160> NUMBER OF SEQ ID NOS: 7

<210> SEQ ID NO 1
<211> LENGTH: 51
<212> TYPE: DNA
<213> ORGANISM: Homo sapiens

<400> SEQUENCE: 1
cagcgtttta cagatgaaga atccarggta cagagatgtc aaagggcttg g              51

<210> SEQ ID NO 2
<211> LENGTH: 51
<212> TYPE: DNA
<213> ORGANISM: Homo sapiens

<400> SEQUENCE: 2
gttaaaattc aaacttttgt ctgtaygtgt atgatttcca agctatttct a              51

<210> SEQ ID NO 3
<211> LENGTH: 51
<212> TYPE: DNA
<213> ORGANISM: Homo sapiens

<400> SEQUENCE: 3
ggctaatatt aacactgaca tctgcmaagt aatattggaa tggacatcca a              51

<210> SEQ ID NO 4
<211> LENGTH: 51
```

```
<212> TYPE: DNA
<213> ORGANISM: Homo sapiens

<400> SEQUENCE: 4
aacgtagaaa tctgtgaaac tctatmcttc gtgtcagttt taacattgtg t      51

<210> SEQ ID NO 5
<211> LENGTH: 51
<212> TYPE: DNA
<213> ORGANISM: Homo sapiens

<400> SEQUENCE: 5
cccaccttag ttagatacgt tactcyttat cctcctgcct ccatttccca a      51

<210> SEQ ID NO 6
<211> LENGTH: 51
<212> TYPE: DNA
<213> ORGANISM: Homo sapiens

<400> SEQUENCE: 6
tactggtgat atgtaagagt gaacayggcc tttcaaaggg tgaatcaaaa t      51

<210> SEQ ID NO 7
<211> LENGTH: 51
<212> TYPE: DNA
<213> ORGANISM: Homo sapiens

<400> SEQUENCE: 7
cttcactcag tcaaaaaatt tcatgytaag ccagccaggt ttacacacat t      51
```

TIME WINDOW-BASED PLATFORM FOR THE RAPID STRATIFICATION OF BLUNT TRAUMA PATIENTS INTO DISTINCT OUTCOME COHORTS

CROSS REFERENCE TO RELATED APPLICATIONS

This application is a continuation of U.S. Patent Application Ser. No. 15/971,519, filed May 4, 2018, which claims the benefit of U.S. Provisional Patent Application No. 62/502,018, filed May 5, 2017, each of which is incorporated herein by reference in its entirety.

STATEMENT REGARDING FEDERAL FUNDING

This invention was made with government support under Grant No. GM053789 awarded by the National Institutes of Health. The government has certain rights in the invention.

SEQUENCE LISTING

The Sequence Listing associated with this application is filed in electronic format via EFS-Web and is hereby incorporated by reference into the specification in its entirety. The name of the text file containing the Sequence Listing is 6527_1803176_ST25.txt. The size of the text file is 1,500 bytes, and the text file was created on May 2, 2018.

Trauma is the leading cause of death and disability for individuals under age of 55 years in the United States. With improvements in pre-hospital and trauma systems, the outcome landscape following traumatic injury has shifted from mortality to complications such as nosocomial infection (NI) and multiple organ dysfunction syndrome (MODS), which are associated with a state of persistent critical illness. This state is defined by prolonged intensive care unit (ICU) and hospital length of stays (LOS), discharge to long-term care facilities, and a continued increased risk for complications and death after discharge. The current clinical challenge is that of reducing short- and long-term morbidity through early-targeted interventions. Clinical trials that incorporate early patient stratification could increase the likelihood of identifying effective therapies by enriching for patients that are likely to develop adverse outcomes (e.g., features of persistent critical illness). It is widely accepted that both short- and long-term morbidity are, in part, the result of a dysregulated immune response. Previous work has established that many aspects of this dysregulated response can be recognized early following severe injury including unique gene expression patterns and inflammatory mediator levels.

The design of early interventional trials for trauma presents some unique opportunities and a number of major obstacles. Compared to many other major causes of morbidity and mortality in the critical care setting, trauma is unique in that the time of onset can be established with considerable precision. Hence, the timing of interventions can be exact relative to the evolution in the patient's pathophysiology and availability of potential therapeutic targets. However, the need for rapid intervention also imposes major challenges both in the hospital and in the design of clinical trials. Challenges include the identification of meaningful outcome-based endpoints, in addition to mortality, and the validation of methods to expeditiously stratify for patients most likely to benefit from a given intervention.

SUMMARY

In one aspect of the invention, a method of managing a trauma injury patient or a method of determining risk of multiple organ dysfunction in a trauma injury patient, is provided. The method comprises: obtaining within a window of time after injury a patient's values for members of a panel of biomarkers, clinical variables, and/or genetic polymorphisms that are, as a group, able to segregate, using one or more statistical and/or mathematical methods on a data set of a statistically-significant size, patients at least into group of patients that experience high risk, and patients that experience low risk, of multiple organ dysfunction with clinically-acceptable specificity and selectivity; determining, using a computer-implemented method, a value for the obtained patient's values for each member of the panel of biomarkers, clinical variables, and/or genetic polymorphisms against a set of stored values for a statistically-significant number of patients, and calculating a representation of those values to produce a panel value; determining, using a computer-implemented method, if the panel value for the patient is within a range of panel values for the set of stored values within which patients experience a clinically-relevant risk of multiple organ dysfunction or nosocomial infection; and producing, using a computer-implemented method, an output indicating whether the patient is expected to experience a risk of multiple organ dysfunction or nosocomial infection.

In aspects, a system is provided, comprising a computer, instructions for performing the method of the preceding paragraph, and a computer-readable medium comprising the set of stored values for a statistically-significant number of patients for panel of patient biomarkers, clinical variables, and/or genetic polymorphisms.

BRIEF DESCRIPTION OF THE DRAWINGS

FIG. 2 depicts a Time Window-based scheme for the design of trials in trauma patients incorporating early stratification. The initial time interval is defined as the "diagnostic window," which represents "Time Period 1" where patient-specific information is gathered and used for the stratification of patients into interventional cohorts. Stratification would follow the diagnostic window and lead into the interventional window (Time Period 2). In a trial, the length of this window would be determined by the duration of the intervention. The third time window (Time Period 3) incorporates the measurement of a primary end point, that if reduced in magnitude should theoretically correlate with improved short- and long-term outcomes. In this study, we hypothesized that this endpoint could be used to identify the prognostic variables to be used in Window 1. The next phase in the sequence, "Time Period 4", is the time interval where in-hospital outcomes data are gathered as secondary endpoints. Examples of such secondary, in-hospital end points are ICU LOS, total hospital LOS, and incidence of nosocomial infection (NI). The final phase in this scheme, defined by "Time Period 5", is the post-discharge timeframe in which additional secondary outcomes reflecting patients' long-term recovery relative to "pre-injury" status and overall resource utilization are measured. Such outcomes could include information on discharge disposition, unplanned readmissions, and long-term quality of life. Ideally, both the in-hospital endpoints and the long-term outcomes (Time Periods 4 and 5, respectively) would be impacted by interventions that reduce the severity of the primary endpoint.

FIG. 3 is a table providing MOD score metrics as described in the examples below.

FIG. 4 is a table providing the results of Decision List analysis performed on the top-ranked metrics to define the MOD score cut-off values that segregated the greatest number of patients with the highest incidence of NI.

FIG. 5 is a table providing analysis on 25 routine admission clinical variables, as described in Example 1, below.

FIG. 8 is a table identifying the seven SNPs associated with increased trauma mortality (SEQ ID NOs:1-7, respectively).

FIG. 10 is a table providing demographics of severely injured rs2065418 AA patients vs. control.

DETAILED DESCRIPTION

Figure 1:
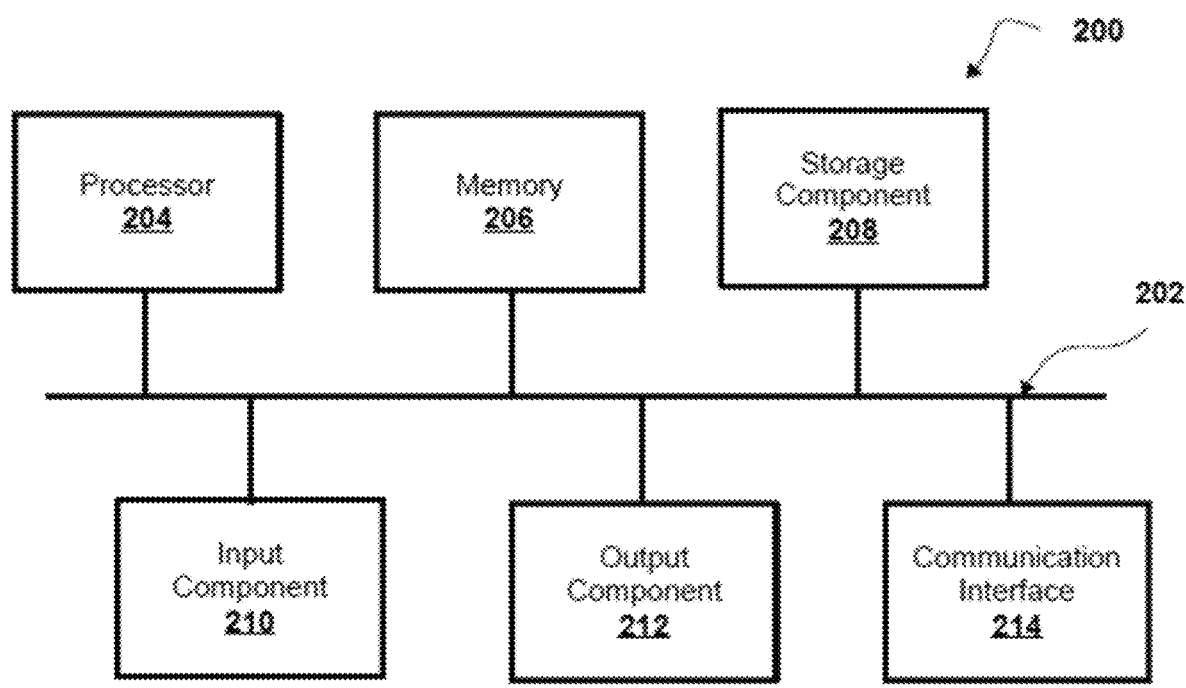
FIG. 1 is a diagram of example components of a computer device.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "patient" or "subject" refers to members of the animal kingdom including but not limited to human beings and "mammal" refers to all mammals, including, but not limited to human beings.

As used herein, the "treatment" or "treating" of a wound or defect means administration to a patient by any suitable dosage regimen, procedure and/or administration route an amount of a composition, device or structure effective to, and with the object of achieving a desirable clinical/medical end-point, including preventing MODS or NI in a patient.

An intensive care unit (ICU) is an organized system for the provision of care to critically ill patients that provides intensive and specialized medical and nursing care, an enhanced capacity for monitoring, and multiple modalities of physiologic organ support to sustain life during a period of acute organ system insufficiency. Although an ICU is based in a defined geographic area of a hospital, its activities often extend beyond the walls of the physical space to include the emergency department, hospital ward, and follow-up clinic, and includes primary (level 1), secondary (level 2), and tertiary (level 3) ICUs as described in Marshall, J C et al. (What is an intensive care unit? A report of the task force of the World Federation of Societies of Intensive and Critical Care Medicine. *Journal of Critical Care* 37 (2017) 270-276).

A MOD Score is a classification system devised to assess risk of intensive care unit (ICU) mortality. One example of a MOD Score is the Marshall MOD Score, originally described in Marshall J C, et al. (Multiple organ dysfunction score: a reliable descriptor of a complex clinical outcome. Crit Care Med. 1995 October; 23(10):1638-52). Other MOD Scores include the Denver score or SOFA score, as are broadly-known in the art. Of note, the examples below utilize a Marshall MOD Score. Because each manner of calculating a MOD score is different, the relevant number values for thresholds and ranges described herein will vary, depending on the methodology. In one aspect, a Marshall MOD score of 3 will have an equivalent using the other MOD score methodologies, and might be referred to as, for example and without limitation, "a Marshall MOD score of 3 or an equivalent thereof". Blunt trauma is non-penetrating trauma, and its severity can be rated on a scoring system. In one aspect, severity is rated based on the broadly-known and utilized Injury Severity Score (ISS), with a score of 15 or higher being the common cutoff for major trauma, and for severe trauma or blunt trauma an ISS score of 25 or greater.

An allele is one of two or more forms of a gene or a genetic region. A population or species of organisms typically includes multiple alleles at each locus distributed among various individuals; except very rarely, each individual can have only two alleles at a given locus.

Allelic variation at a locus is measurable as the number of alleles (polymorphisms) present, or the proportion of heterozygotes in the population. Alleles arise from differences in a nucleotide sequence at a given locus, and such difference can include insertions, deletions and/or substitutions. A single-nucleotide polymorphism (SNP) is a DNA sequence variation that occurs when a single nucleotide (A, T, C, or G) in the genome sequence is altered. An SNP differs between members of a species, or between paired chromosomes in an individual (heterozygous)—in which case it is said that there are two alleles. Allelic variants, e.g., SNPs may be silent (synonymous), or non-synonymous if they produce a different protein sequence. SNPs and other allelic variants are well catalogued in multiple on-line resources, including the National Center for Biotechnology Information (NCBI) SNP database, dbSNP.

Where it is stated a polymorphism is homozygous or heterozygous for a nucleobase at a specified SNP, it is meant, in reference to the sequences identified in the table of FIG. 8, the identified sequence corresponding to the designated SNP includes the specified polymorphic base at the designated position/locus for the SNP. As an example, if a polymorphism is identified as homozygous for a C at rs2065418, it is meant that, for both alleles in a patient, the patient's genome at chromosome 11, p14.1, includes the corresponding sequence with a C at the polymorphic site.

Linkage disequilibrium refers to the instance where alleles occur together more often than can be accounted for by chance, typically indicating that the two alleles are physically close on the DNA strand. As indicated below, seven SNPs were identified as being relevant to patient survival after blunt trauma. As would be apparent to one of ordinary skill, polymorphisms in linkage disequilibrium with any of the seven identified SNPs, such that they can be considered associated to any useful statistical significance, also can be considered to be useful for the same purpose. As such, as an example, a "C at rs2065418 or an associated polymorphism thereof" includes both the C at rs2065418 as well as any other polymorphisms that associate with the C at rs2065418 to sufficient statistical significance, e.g., D, D', or $R^2$ value, as are broadly-known in the genomics and genetics fields, so as to be diagnostically predictive in the context of the present invention (e.g., D'>0.75 or $R^2$>0.75). Further details relating to linkage disequilibrium are provided in Example 2, below.

The methods described herein are useful in determining if a trauma patient, such as a blunt trauma patient, has a significant and clinically-relevant risk of developing multiple organ dysfunction syndrome (MODS) as a consequence of the injury. A blunt trauma patient may also have other injuries. These methods improve computer processing speed, memory usage, and overall computer efficiency, along with providing a solution to a difficult problem—that of quickly, e.g., within 24 hours of injury, and effectively classifying blunt trauma patients as to their likelihood of developing MODS. The methods described herein involve obtaining patient information, e.g., within the first 24 hours after injury, relating to a panel of biomarkers, clinical variables, and/or genetic polymorphisms, and analyzing the obtained values in a computer method, as described herein, using one or more statistical or mathematical models capable of classifying patients, such as, for example, multivariate regression models, dynamic models, mechanistic models that recapitulate a patient's biology, or dynamic profiling methods. In one aspect, at least a ranking algorithm is used to determine if the ranking of patient's values, when ranked in comparison to a sufficiently large, statistically-significant set of stored patient values, is greater than a threshold ranking capable of differentiating patients having a significant risk of developing MODS from patients who do not. In one aspect, the ranking is a rank sum (e.g., Wilcoxon rank sum) method.

By "statistically significant," it is meant a result that is not considered to be by chance, and therefore in reference to underlying data and processes used to produce a result, those data are sufficient to generate a statistically significant result. In aspects, in the context of the methods described herein, a statistically significant result is a result of sufficient certainty to be clinically-relevant and therefore acceptable to medical practitioners as a basis to make a learned medical decision. Thus, a statistically significant set of stored values for use in the ranking methods would have a sufficiently large number of patient values, such as values from 100, 200, 300, 400, or a larger number of patient, such that the ranking method described herein produces a result with sufficient reliability for clinical reliance.

As an initial step in methods described herein, a panel of biomarkers, clinical variables, and/or genetic polymorphisms is determined. The patient's values for members of a panel of biomarkers and clinical variables are obtained within a window of time (time frame) starting immediately after injury and for a relevant time thereafter. In aspects, the window of time is from immediately after injury to one month after injury, such as ranging from one minute, five minutes, ten minutes, 15 minutes, 30 minutes, 1 hour, or two hours after injury to one hour, two hours, three hours, four hours, five hours, six hours, seven hours, eight hours, nine hours, 10 hours, 12 hours, 18 hours, 24 hours, 36 hours, 48 hours, one week, or two weeks after injury, including increments therebetween, such as from 1 minute to 48 hours after injury, from 5 minutes to 36 hours after injury, from 10 minutes to 24 hours after injury, or within 24 hours of injury.

As shown in the Example below, a stored dataset including patient biomarkers, clinical variables, and/or genetic polymorphisms and outcomes was first utilized to identify a meaningful endpoint predictive of MODS and/or NI. As an example, using those statistical methods, the average Marshall MOD score for patients on days 2-5, inclusive ($aMOD_{D2-D5}$), was determined to be a good segregator of patients likely to suffer MODS, with a value of greater than three categorizing patients into a High $aMOD_{D2-D5}$ group. A panel of biomarkers, clinical variables, and/or genetic polymorphisms that can be determined within 24 hours of patient admission or injury, was then identified as having the ability to segregate patients into a High $aMOD_{D2-D5}$ group ($aMOD_{D2-D5}$>3) or a Low $aMOD_{D2-D5}$ group ($aMOD_{D2-D5}$≤3), using computer-implemented statistical methods. The identified panel-interleukin 10 (IL-10), MCP-1/CCL2, Cl, $CO_2$, serum creatinine, partial thromboplastin time (PTT), and platelet counts—was found to be effective using ranking algorithms, in effectively segregating blunt trauma patients into a High aMOD$_{D2-D5}$ group (aMOD$_{D2-D5}$>3) and a Low aMOD$_{D2-D5}$ group (aMOD$_{D2-D5}$≤3). This result was generated using a data set of values obtained from 376 patients. By comparing newly-obtained values for a blunt trauma patient or patients to the existing, stored data set, and applying at least a ranking algorithm to those data, a patient can be classified, with satisfactory specificity and selectivity, into High aMOD$_{D2-D5}$ group (high risk of MODS or NI) and a Low aMOD$_{D2-D5}$ group (low risk of MODS or NI). Use of a ranking algorithm on the data set in the examples below, yielded a rank-sum threshold value of 61% of the maximum rank sum value, which was capable of effectively stratifying patients in to the High aMOD$_{D2-D5}$ group and the Low aMOD$_{D2-D5}$ group.

In another example, below, Fuzzy C-means Clustering Analysis (FCM), followed by eight common Clustering Validation Indices (CVI), was used to segregate an aMOD$_{D2-D5}$ group into four, as opposed to two relevant clusters with different patient outcomes, such as patterns of organ dysfunction which can be used to differentially treat patients falling in each class. Further, a set of biomarkers, including IL-6, MCP-1, IL-10, IL-8, IP-10, sST2, and MIG, were elevated differentially over time across the clusters, and based on the biomarker profile can be used to effectively separate blunt trauma injury patients into treatment classes or study cohorts.

As would be appreciated by those of ordinary skill in the art, the data set used to obtain these results can be enlarged through the addition of additional and appropriate new patient data that optionally excludes data following any intervention provided as a result of the methods described herein, so as to avoid bias. The use of the Marshall MOD Score, and the related threshold of aMOD$_{D2-D5}$, 3, or clusters, are merely exemplary, and other MOD scoring methods (e.g., Denver or SOFA scores), as are broadly-known in the art, and appropriate cutoffs determined statistically and/or mathematically, e.g., as in the methods below, may be utilized to determine a suitable end-point for establishing a panel of biomarkers, clinical variables, and/or genetic polymorphisms, obtained within 24 hours of injury, for use in classifying patients for risk of MODS or NI, or even particular organ dysfunctions. Likewise, through use of appropriate statistical methods, e.g., as shown in the examples below, or otherwise, an optimized panel of biomarkers, clinical variables, and/or genetic polymorphisms may be determined that are different from, or include one, two, three, four, five, six, or all seven of IL-10, MCP-1/CCL2, Cl, $CO_2$, creatinine, PTT, and platelet counts and one or more additional markers. For example, as identified below, certain genetic polymorphisms (SNPs) have been found to be associated with higher mortality and altered Th17 responses following blunt trauma.

Although the genetic polymorphisms provide binary (presence/absence) scores, and are not likely suitable for treatment, e.g., ranking, in the same manner as non-binary values, e.g., obtained from laboratory results, statistical optimization methods can be used, e.g., as described in the examples below, to best determine how to incorporate those binary values into the ranking system, or prior to or subsequent to the ranking, e.g., by providing a suitable multiplier of a Wilcoxon rank-sum value. Such a suitable multiplier might be optimized using the data set described in the examples, and the ability of any such value to classify patients can be readily ascertained. In a ranking method, for all variables, the values are ranked in order of their contribution to a High aMOD$_{D2-D5}$ group and the Low aMOD$_{D2-D5}$ group, ranging from the lowest rank value, corresponding to the least contribution to a High aMOD$_{D2-D5}$ phenotype, to the highest rank value, corresponding to the greatest contribution to a High aMOD$_{D2-D5}$ phenotype. Rankings may be generated in any order, e.g., from lowest to highest, from highest to lowest, from distance from a specified value, or otherwise, as a reflection of the contribution of the value for the variable to the High aMOD$_{D2-D5}$ phenotype.

In one aspect, as indicated herein, for the identified panel—IL-10, MCP-1/CCL2, Cl, $CO_2$, creatinine, PTT, and platelet counts—a threshold value of 61% of the maximum rank sum was selected to discriminate between the High aMOD$_{D2-D5}$ group and the Low aMOD$_{D2-D5}$ group. As such, for different panels, a different threshold may be used, for example, in the range of from 55% to 65% of the maximum rank-sum value, e.g., at least 55%, 56%, 57%, 58%, 59%, 60%, 61%, 62%, 63%, 64%, or 65% of the maximum rank-sum for the data set.

Although a rank-sum method was used in the examples below, other ranking methods may be utilized to generate a ranking of parameters. The sum of the ranks is only one manner of generating a representation of the ranking of each parameter, and the set of parameters as a whole. Therefore, the ranking and rank-sum are described herein as an example of a rank value for each biomarker, clinical variable, and/or genetic polymorphism, and a panel rank value is the combined representation of the combined value of all biomarkers, clinical variables, and/or genetic polymorphisms used to rank a test sample, e.g., from a patient to be evaluated.

The methods described herein for classification of patients, e.g., into cohorts, comprise generation of an output that is readable by, e.g., a computer, physician, or patient, such as a printout, or a video display image. The results of the classification can have any of a number of uses. In one aspect, the classification of the patient dictates the treatment of the patient. For instance, the treatment may include an immune modifying or anti-inflammatory intervention, such as administration of anti-inflammatory compounds or compositions, such as a drug product or therapeutic agent, monitoring the patient for an inflammatory response, an elevated Th17 response, and/or regular testing and monitoring of MOD score. In another aspect, the method is used to segregate a population of blunt trauma patients into cohorts for an interventional trial, such as for testing a drug product or other intervention for safety and efficacy for treatment or prophylaxis of MODS or NI in blunt trauma patients, e.g., for submission of data to a regulatory agency.

An anti-inflammatory compound is a therapeutic agent that is able to reduce inflammation in a patient. In aspects, the anti-inflammatory agents are able to reduce systemic inflammation associated with sepsis, systemic inflammatory response syndrome, or multiple organ dysfunction syndrome. Useful anti-inflammatory agents used for treatment of systemic inflammation include: low dose corticosteroids, drugs and/or supplements to lower Th17 response, such as, antibodies or small molecules targeting interleukin-6, interleukin-17A, or interleukin-23. Alternatively or in addition to an immune modulator, an antibiotic may be administered, e.g., prophylactically, to prevent a nosocomial infection in the patient. Immune modulating therapeutic agents and antibiotics are broadly-known.

In aspects, therapeutic agents that may be used for treatment of a patient include, without limitation: anti-inflammatories, such as, without limitation, NSAIDs (non-steroidal anti-inflammatory drugs) such as salicylic acid, indomethacin, sodium indomethacin trihydrate, salicylamide, naproxen, fenoprofen, sulindac, diflunisal, diclofenac, indoprofen, sodium salicylamide, anti-inflammatory cytokines, and anti-inflammatory proteins, anti-inflammatory antibodies or binding reagents such as antibody fragments or aptamers, or steroidal anti-inflammatory agents, e.g., glucocorticoids (see below); antibiotics, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulfate, Zn-pyrithione, ciprofloxacin, norfloxacin, afloxacin, levofloxacin, gentamicin, tobramycin, neomycin, erythromycin, trimethoprim sulfate, polymixin B, and silver salts such as chloride, bromide, iodide, and periodate; immunosuppressants; and glucocorticoids, such as, without limitation, hydrocortisone, betamethasone, dexamethasone, flumethasone, isoflupredone, methylprednisolone, prednisone, prednisolone, and triamcinolone acetonide.

In aspects, the methods described herein are implemented by use of a computer in any suitable form. Referring now to FIG. 1, FIG. 1 is a diagram of example components of a device 200. As shown in FIG. 1, device 200 may include a bus 202, a processor 204, memory 206, a storage component 208, an input component 210, an output component 212, and a communication interface 214.

Bus 202 may include a component that permits communication among the components of device 200. In some non-limiting embodiments or aspects, processor 204 may be implemented in hardware, firmware, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read only memory (ROM), and/or another type of dynamic or static storage device (e.g., flash memory, magnetic memory, optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally, or alternatively, input component 210 may include a sensor for sensing information (e.g., laboratory instrumentation, a global positioning system (GPS) component, an accelerometer, a gyroscope, an actuator etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmitter, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a WiFi® interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally, or alternatively, hardwired circuitry may be used in place of or in combination with software instructions to perform one or more processes described herein. Thus, embodiments or aspects described herein are not limited to any specific combination of hardware circuitry and software.

The number and arrangement of components shown in FIG. 1 are provided as an example. In some non-limiting embodiments or aspects, device 200 may include additional components, fewer components, different components, or differently arranged components than those shown in FIG. 1. Additionally, or alternatively, a set of components (e.g., one or more components) of device 200 may perform one or more functions described as being performed by another set of components of device 200.

The method described here includes obtaining values for biomarkers, clinical variables, and/or genetic polymorphisms from a trauma patient, e.g., a blunt trauma patient, within a time window of from 1-24 hours of injury. "Obtaining" such values includes, but does not necessarily require, conducting laboratory tests to produce the values. Thus, in one aspect, "obtaining" includes acquiring data values produced by another party or person, such as a laboratory, for input for the computer-based processing of the data, and in another aspect, includes performing the assays and then inputting the data into a computer. Genetics data can be obtained by any useful test, such as by a polymerase chain reaction, probe-based assays, resequencing, or microarray methods, such as by use of a custom microarray designed for the present method, are conducted according to any suitable methodology, as are broadly-known for any of the preceding.

Clinical laboratory scientists and technicians would readily know how to obtain patient samples, and values for the panel of variables, such as biomarkers, clinical variables, and/or genetic polymorphisms, e.g., for IL-10, MCP-1/CCL2, Cl, $CO_2$, serum creatinine, PTT, and platelet counts. The clinical variables, Cl, $CO_2$, creatinine, PTT, and platelet counts, are routinely-tested in patients, and those of ordinary skill in the art would know how to obtain such values as a matter of course in virtually any clinical laboratory. The assays may be included in commercially-available laboratory testing products, including automated products. IL-10 (interleukin 10) is a well-characterized protein, and one of ordinary skill would know how to obtain serum values for the compound, as many assays are available, such as the Human IL-10 Luminex® Performance Assay. Likewise, monocyte chemoattractant protein 1 (MCP-1), also known as chemokine (C—C motif) ligand 2 (MCP-1/CCL2), is a well-characterized protein, and one of ordinary skill would know how to obtain serum values for the compound, as many assays are available, such as the Human CCL2/MCP-1 Luminex® Performance Assay. Assays for other biomarkers, such as IL-6, MCP-1, IL-10, IL-8, IP-10, sST2, and MIG, are described in the examples below. Other assays for biomarkers, e.g., serum biomarkers, are known and are broadly, commercially available and/or described in the literature, including ELISA and RIA assays.

In one aspect, the assay is a Luminex® assay (R&D Systems), which uses addressable, fluorescently-tagged beads attached to an antibody for capturing the analyte of interest. A second, biotinylated antibody also specific to (specifically binding) the analyte of interest is bound to the beads, and then fluorochrome-tagged streptavidin is used to label the biotin. Particles are identified by fluorescence of the fluorescently-tagged beads and bound analyte, e.g., IL-10, is identified and quantified by the fluorescence of the fluorochrome of the fluorochrome-tagged streptavidin on the beads, e.g., using a dual-laser flow-based detection instrument, such as the Luminex® 100™, Luminex 200™ or BioRad® BioPlex® analyzers, or imaged on a surface using magnetic beads and a dual LED device, such as the Luminex® MAGFIX® Analyzer. Such assays are calibrated and can be used to quantify biomarkers such as IL-10 and MCP-1/CCL2 in serum. Luminex® assays can be multiplexed (e.g., simultaneously tested for as IL-10 and MCP-1/CCL2 in the same vessel) using separately-addressable beads. Genetic markers, such as the SNPs described herein, are identifiable by any useful method, for instance, as in the examples below, by use of microarrays, such as the Illumina® Infinium CoreExome-24 v1.1 BeadChip (Illumina®).

Example 1

To identify meaningful outcome-based endpoints, in addition to mortality, and the validation of methods to expeditiously stratify for patients most likely to benefit from the intervention, a time window-based construct was designed. As depicted schematically in FIG. 2, five sequential time intervals are identified, each representing a defined phase in the design of interventional trials are shown. In the first window, information is gathered for the purpose of patient stratification prior to an interventional window. Subsequent windows encompass a primary outcome as well as short- and long-term secondary outcomes. This scheme defines the sequence of the windows, but does not place limits on the duration of the windows, the information gathered in each time frame, or the interventions to be performed. In order to use this time window model, a set of statistical methods would be needed to identify variables obtained in the diagnostic window which could prognosticate for an adverse outcome measured in the primary outcome window. To develop a set of such methods, we established a threshold value for a MODS-based outcome to serve as a primary outcome, using data from a derivation cohort comprised of severely injured blunt trauma patients. This parameter segregated a subset of High MODS patients that developed significantly higher complication rates and longer ICU LOS, as well as unique inflammatory biomarker patterns. Statistical methods were then developed to identify variables from data sets comprised of routine clinical data and circulating levels of 30 inflammation biomarkers that prognosticated for the High MODS outcome. These methods identified a subset of variables that predicted High MODS in both the derivation cohort and a separate validation trauma patient cohort with high sensitivity. The windows scheme combined with the statistical methods described here could be an effective platform for the design of clinical trials that incorporate early patient stratification following injury.

Materials and Methods

Patient Enrollment, Sampling, and Clinical Data Collection

Patients eligible for enrollment were victims of blunt trauma, at least 18 years of age and admitted to the ICU. Exclusion criteria included isolated head injury, pregnancy, penetrating trauma, or expected duration of survival <24 h. Demographic and clinical data were abstracted from the inpatient electronic medical record and the trauma registry database.

Analysis of Inflammation Biomarkers

Three blood samples, starting with the initial blood draw upon arrival, were collected into citrated tubes via central venous or arterial catheters and assayed within the first 24 h following injury and then daily from days 1 to 5 post-injury. The blood samples were centrifuged, and plasma aliquots were stored in cryopreservation tubes at −80° C. for subsequent analysis of inflammatory mediators (a total of 30 biomarkers in the derivation cohort and 19 biomarkers in the validation cohort). The human inflammatory MIL-LIPLEX™ MAP Human Cytokine/Chemokine Panel-Premixed 26 Plex, MILLIPLEX™ MAP Human Th17 Panel (Millipore Corporation, Billerica, MA), Luminex® 100 IS analyzer (Luminex, Austin, TX), and MAGPIX® system (MilliporeSigma, Austin, TX) were used to measure plasma levels of interleukin (IL)-1β, IL-1 receptor antagonist (IL-1 RA), IL-2, soluble IL-2 receptor-α (sIL-2Rα), IL-4, IL-5, IL-6, IL-7, IL-8 (CCL8), IL-9, IL-10, IL-13, IL-15, IL-17A, IL-17E/IL-25, IL-21, IL-22, IL-23, IL-33, interferon (IFN)-γ, IFN-α, IFN-γ inducible protein (IP)-10 (CXCL10), monokine induced by gamma interferon (MIG; CXCL9), macrophage inflammatory protein (MIP)-1α (CCL3), MIP-1β (CCL4), monocyte chemotactic protein (MCP)-1 (CCL2), granulocyte-macrophage colony stimulating factor (GM-CSF), Eotaxin (CCL11), and tumor necrosis factor alpha (TNF-α). The Luminex™ system was used in accordance to manufacturer's instructions. Plasma levels of soluble ST2 (sST2) were measured by ELISA according to the manufacturers' instructions (R&D Systems, Minneapolis, MN).

Study Design and Optimization of a MOD Score-Derived Parameter

The derivation and internal validation cohorts were taken from a database of 493 blunt trauma patients who were admitted to the ICU of the UPMC Presbyterian University Hospital, a Level 1 trauma center. The validation cohort consisted of 65 blunt trauma survivors who were admitted to the ICU of the Indiana University Health Methodist Hospital (also a Level 1 trauma center). The clinical database and biobank of both cohorts were maintained prospectively over an eight and two-year period, respectively.

Patients with incomplete MOD scores for D2 to D5 (due to discharge from the ICU), or that died prior to discharge, were excluded in order to capture a complete data set for the derivation group. Therefore, a sample size of 376 patients from the University of Pittsburgh was used as the derivation data set. The remaining 117 patients including 19 that died prior to discharge and 98 that were discharged from the ICU in less than 5 days were assessed separately. Sixty-five patients from Indiana University were used for external validation of the model.

To optimize the MOD score-related parameter within D2-D5 a MOD metric that best correlated with the prevalence of nosocomial infection (NI, based on the United States Centers for Disease Control (CDC) clinical criteria) was identified. First, MOD scores were calculated using three separate methods: 1) Individual MOD score at each single day: MOD2, MOD3, MOD4, and MOD5; 2) Maximum MOD score (mMOD) between day i and day j, inclusive: mMOD2-3, mMOD2-4, mMOD2-5, mMOD3-4, mMOD3-5, and mMOD4-5; and 3) Average MOD score (aMOD) between day i and day j, inclusive: aMOD2-3, aMOD2-4, aMOD2-5, aMOD3-4, aMOD3-5, and aMOD4-5. Second, the percentage of patients with NI at different MOD score values were plotted for each type of MOD score calculation, and the optimal category was selected by analyzing the area under the curve (AUC) of the receiver operating characteristic (ROC) of the NI outcome. The non-parametric Spearman correlation of the ICU and total hospital length of stays outcomes were also analyzed using IBM SPSS Statistics, Version 23 (IBM Corp., Armonk, NY) and Python SciPy library. This analysis identified metrics that averaged MOD scores over multiple days and specifically MOD score averaged over D2-D5 ($aMOD_{D2-D5}$) as the top metric that best correlated with NI rates, ICU stay, and total length of stay (LOS) (FIG. 3). NI was chosen to define the MOD score threshold because its definition is standardized across multiple institutions (based on the CDC clinical criteria) and can be dichotomized into a binary variable (e.g., either with or without NI).

Decision List Analysis

Decision list (DL) analysis was used to determine the optimal MOD score threshold value for $aMOD_{D2-D5}$ based on which group of patients who have statistically significant high probability of NI can be identified. The decision rule split algorithm of DL is used to generate high response segments from a single attribute. It performs an exhaustive and iterative search by starting with the calculation of the response probability $p_i$ (the probability of NI) for each category in the attribute (e.g., MOD score metrics). Using the result, the algorithm finds the local maxima of $p_i$ to create a segment set. Then, the segment $S_{L,R}$ with the highest response probability $p_{S_{L,R}}$ is selected and validated by the following conditions: 1) the size of segment exceeds the minimum segment size criterion; 2) its response probability is significantly higher than that for the overall sample as indicated by non-overlapping confidence intervals; and 3) extending the segment would lower the response probability. If the segment $S_{L,R}$ passes the validation step, it will be added to the result set and any segments $S'_{L,R}$ from result set that have $S_{L,R}$ as parent will be removed. The segment $S_{L,R}$ will then be extended by adding adjacent categories in the attribute and returned to the segment set. If R−L+1=M or $p_{S_{L,R}} \leq p_{S_{L,M}}$, where M is the total number of categories in the attribute, it will remove the segment $S_{L,R}$ from segment set and choose another segment with highest response probability. The algorithm repeats the process of selection, validation and extension in the segment set until no new segment can be found for the result set. The DL analysis was performed on the derivation dataset using the DL node in IBM SPSS Modeler, Version 17 (IBM Corp., Armonk, NY). The detailed algorithm and formula for calculating the confidence interval are listed in the IBM SPSS Modeler 17 Algorithms Guide, page 105-112. The maximum segment number was set to equal to one in the model setting of the DL node. The DL analysis indicated that the optimal cut-off value for MOD score was 3 with which to segregate patients into two MOD-based groups, namely Low $aMOD_{D2-D5}$ group (≤3) and High $aMOD_{D2-D5}$ group (>3).

Dynamic Network Analysis (DyNA)

We carried out DyNA between the High and Low $aMOD_{D2-D5}$ groups. The goal of this analysis was to gain insights into the temporal dynamic changes in network connectivity and complexity of the post-traumatic inflammatory response between the High and Low $aMOD_{D2-D5}$ groups. The mathematical formulation of this method is to calculate the correlation among variables (inflammatory mediators) that can be used to examine their interdependence. To do so, inflammatory mediator networks were created in adjacent 8-h time periods over the first 24 h (0-8 h, 8-16 h, and 16-24 h) and then from day 2 to day 5 (inclusive) using MATLAB® (The MathWorks, Inc., Natick, MA) as described previously. Connections, defined as the numbers of trajectories of plasma inflammatory mediators that move in parallel, were created if the Pearson correlation coefficient (independent from the correlation coefficients calculated for the model development) between any two nodes (inflammatory mediators) at the same time interval was greater or equal to a threshold of 0.7.

Development of Statistical Prediction Models

In addition to available packages in R and S plus that include LASSO Sparse Logistic models and decision trees, we developed mathematical and statistical methods to identify the admission variables derived from routine clinical data and circulating inflammation biomarker levels that best prognosticated for the $aMOD_{D2-D5}$ score parameter. These models were developed using R (The R Project for Statistical Computing) and S-PLUS (Insightful Corporation. Seattle, WA).

Statistical Prediction Models

For qualitative purposes, the MODScore was dichotomized into 0 and 1 signifying the Low $aMOD_{D2-D5}$ (≤3) and High $aMOD_{D2-D5}$ (>3), respectively. Three prognostic models were developed for each of the two outcomes (e.g., Low and High $aMOD_{D2-D5}$) based on admission variables obtained from the first blood draw samples within 24 h post-injury: (1 inflammation biomarker model, which included 30 admission biomarkers; (2 clinical variables model, which included 25 admission clinical parameters; and (3 combined biomarkers and clinical variables model, which included both the admission biomarkers and clinical variables. The derivation cohort (355 patients with complete admission clinical and biomarker data; 287 with Low aMOD$_{D2-D5}$ and 68 with High aMOD$_{D2-D5}$) was used as a training data set to develop the prognostic model, while the validation cohort (65 patients with complete admission clinical and biomarker data; 31 with Low aMOD$_{D2-D5}$ and 34 with High aMOD$_{D2-D5}$) was used to verify the developed model. To assess the accuracy and generalizability of the biomarkers model, we performed an internal cross-validation by randomly selecting 80% of the derivation data to develop the model and then applying the predictive model to the remaining 20% of the data to verify classifications. Due to large patient-to-patient variability with regard to the admission biomarker and clinical data which could not be scaled to lognormal transformations, nonparametric approaches based on ranks were utilized. These included nonparametric correlation and partial correlation tests with the binary response (e.g., 0 for Low aMOD$_{D2-D5}$≤3 and 1 for High aMOD$_{D2-D5}$>3) using Wilcoxon rank sum tests and Spearman correlations. The best 10 variables were chosen using this screening method from which we derived the optimal model that ultimately retained 7 variables out of the 10 variables. The 10 variables yielded 1024 subsets to choose from when selecting for the optimal model. All these regression models were fitted to the data, and thus the final model emerged (e.g., the combined biomarkers and clinical variables model). The way the choice was made was to either include a variable or to exclude it, so the betas in the regression were (by forced choice) either zero or one (this forced sparsity of most betas being zero may be viewed as consequence of the L1 norm applied in LASSO regression). The threshold of rank sum emerges as the cut value that yields the best model fit of the type described above. More specifically, the rank model uses the existing data set (in our case the rank vectors) as reference distribution; the current cutoff rank sum is 1341/2218 or about 61%. When data (the 7 relevant variable readings) from a new patient become available, they are added to the existing data set, ranks are updated with the newly added patient, and a decision for the new patient is made as follows: if the sum of the 7 ranks for the new patient exceeds 1341 the patient is predicted for High MODS, otherwise for Low MODS. The patient now becomes part of the existing data; the rank sum cutoff is updated by refitting the same model to this updated data. This process is then repeated for the next patients' data. These models were developed using R (The R Project for Statistical Computing) and S-PLUS (Insightful Corporation. Seattle, WA).

Data Analysis Using "Off the Shelf" Methods LASSO Sparse Logistic Model

The data includes all the biomarkers and clinical variables (with complete data). It was examined using R packaged programs and libraries for LASSO. Data were log-transformed by t=log(1+y) and standardized, where y are the original responses, to yield log-responses that could be considered Gaussian. A 5-fold cross-validation over 100 iterations/seeds was used to randomly select data samples that comprise the training and test sets. For each iteration/seed a LASSO sparse logistic regression model using an L1 penalty was run on the training data. The predicted beta coefficients for the test fold are then found and all coefficients are obtained after iterating over every fold. The actual R code, including the R Libraries used, is appended below. For each iteration, we have a matrix of beta coefficients for each variable at each fold. The LASSO process zeroes out some coefficients, and each nonzero coefficient that is returned was replaced with a count of 1. We then averaged the number of times (across iterations) that a variable was selected when training a model for each of the five folds to obtain a plot. For example, a value of 5 means that the variable was selected at every iteration. The average AUC value over all iterations is 0.74. The ROC curve shows a sensitivity of 0.70 and specificity 0.64. In a similar manner, and without relying on ranks, using the same variables as in our combined biomarker and clinical variables model, e.g., MCP-1, IL10, CL, $CO_2$, Creatine, Platelets, PTT, we obtain an ROC curve with average AUC value over all iterations of 0.77. The point closest to TPR=1, FPR=0 on the average ROC curve has sensitivity=0.75 and specificity=0.72.

R Script for the LASSO Model

```
# outputs predicted probabilities from sparse logistics regression
and
# counts of significant coefficents
lasso = function(myData, outcome) {
  # create 10 equal size folds
  folds = cut(seq(1, nrow(myData)), breaks=10, labels=FALSE)
  # store coefficients from model
  dat = matrix(NA, nrow = ncol(myData)+1, ncol=nrow(myData))
  rownames(dat) = c("Intercept", colnames(myData))
  # store predicted response
  glmnet_hat = rep(NA, nrow(myData))
  for(i in 1:10) {
    # test indices
    test_idx = which(folds==i, arr.ind=TRUE)
    # run sparse logistic regression model
    myglmnet = cv.glmnet(myData[-test_idx, ], outcome[-test_idx],
family = "binomial", type.measure="deviance", alpha=1,
grouped=FALSE, standardize=FALSE, nfolds=10)
    # coefficients from model
    sigmeta = coef(myglmnet, s = "lambda.min")
    dat[, test_idx] = matrix(sigmeta)
    # predicted probabilities of response from model
    glmnet_hat[test_idx] = predict(myglmnet, myData[test_idx, ],
type="response", s="lambda.min")
  }
  # which covariates were found to be significant
  lasso_counts = dat
  lasso_counts[lasso_counts != 0] = 1
  # how many times a covariate was found to be significant
  count_coef = rowSums(lasso_counts)
  count_coef = count_coef[-1]
  # which covariates were found to be significant (non-zero)
  sig_count_coef = count_coef[which(count_coef != 0)]
  # output: predicted probabilities, counts out of number of
samples of significant coefficients
  out = list(glmnet_hat, sig_count_coef)
  return (out)
}
# import libraries
library(glmnet)
library(ROCR)
library(ggplot2)
# set seed
set.seed(100)
# import dataset
allData = read_csv("~/Desktop/Tata/data.final.csv")
# find missing values in data
miss_idx = which(is.na(allData), TRUE)
# find column means
cM = colMeans(allData, na.rm=TRUE)
# replace NA values by column mean
allData[miss_idx] = cM[miss_idx[, 2]]
# randomly shuffle the data
allData = allData[sample(nrow(allData)), ]
# response
response = allData$MS
# data
myData = as.matrix(allData[2:11])
# run sparse logistic regression model
lass = lasso(myData, response)
```

```
# Plot Counts of Significant Coefficients #
sig_count_coef = lass[[2]]
# create data frame
plotData = data.frame(sig_count_coef)
# create a column containing the covariate names
plotData$covariate = rownames(plotData)
# order rows (covariates) in decreasing order of counts
plotData = plotData[order(plotData$sig_count_coef,
decreasing=TRUE),]
# convert the rows (covariates) to be factors
plotData$covariate = factor(plotData$covariate,
levels=plotData$covariate)
# plot of counts of significant coefficients
p = ggplot(plotData, aes(x=covariate, y=sig_count_coef))
p = p + geom_bar(stat="identity")
p = p + geom_text(aes(label=covariate, angle=90, fontface="bold"),
hjust=-0.1)
p = p + labs(title="Counts (out of 355) of non-zero coefficients",
y="count", x="covariate")
p = p + theme_bw(18)
p = p + scale_y_continuous(breaks = seq(0, 405, 50), limits = c(0,
405))
p = p + theme(axis.text.x = element_blank( ))
p = p + theme(plot.title = element_text(size = 20, face="bold",
hjust=0.5))
p
ggsave("lasso_counts.png", width=10, height=6, dpi=300,
units="in", device="png")
# Find AUC value and Plot ROC curve and Predicted Probabilities #
# predicted probabilites from model
glmnet_hat = lass[[1]]
pred = prediction(glmnet_hat, response)
# area under curve
auc_val = performance(pred, measure="auc")@y.values[[1]]
auc_val
# finding ROC
perf = performance(pred, measure="tpr", x.measure="fpr")
# plot ROC curve
png(filename="roc_curve.png")
plot(perf, main="ROC Curve", lwd=2, cex.axis=2, cex.lab=1.5,
cex.main=3)
abline(a=0, b=1, lwd=2, cex=2)
text(x=0.2, y=0.9, labels=paste("AUC = ", round(auc_val, digits =
2), sep=""), cex=2.5)
dev.off( )
# plot predicted probabilities
predProb=data.frame(predicted_prob=glmnet_hat,
response=as.factor(response))
p = ggplot(predProb, aes(x=response, y=predicted_prob))
p = p + geom_boxplot(outlier.shape = NA)
p = p + geom_jitter(aes(colour=response), position =
position_jitter(width = 0.1), size=3)
p = p + scale_color_manual(labels = unique(response), values =
c("blue", "red"))
p = p + labs(title=paste("Predicted Probabilities"), x="response",
y="predicted probability")
p = p + theme_bw(18)
p = p + theme(plot.title = element_text(size = 20, face="bold",
hjust=0.5))
p = p + theme(plot.subtitle = element_text(size = 14, face="bold",
hjust=0.5))
p
ggsave("lasso_predprob.png", width=10, height=6, dpi=300,
units="in", device="png")
```

CART (Classification and Regression Trees) Decision Tree Analysis

The CART Decision Tree analysis was performed using the Python 2.7 Scikit-learn library (Scikit-learn: Machine Learning in Python, Pedregosa et al., JMLR 12, pp. 2825-2830, 2011). The maximum depth of tree was set as five. The random seed for selecting samples to form the balanced dataset was set as 0, the random state for cross validation in the balanced dataset using stratified shuffle split was set as 0, the random state in the model was set as 0, and the GINI index was applied to measure the degree of impurity and the quality of a split. Given the imbalance of the sample size between the two groups (226:57 in the Low vs High aMOD$_{D2-D5}$, respectively), we sought to train and test the model using a balanced set of 57:57 ratio. The analysis was carried out in the following steps which were repeated 10 times which resulted in a total of 100 pairs of training and testing sets:

Step 1: Form a subset of data A that consists of all 57 High aMOD$_{D2-D5}$ and a random of 57 Low aMOD$_{D2-D5}$ biomarker and clinical data sets. Hence, balancing the sample size for the two classes with the total size of A=114. Then repeat the following Step 2 and Step 3 10 times.

Step 2: Train the Decision Tree (DT) on a randomly selected 80% data (91 samples) from A while keeping the number of samples for the two classes equal (due to the odd number of the sample size of the training data, 46:45 in the Low vs High aMOD$_{D2-D5}$, respectively).

Step 3: Test the DT on the remaining 20% data (11:12 in the Low vs High aMOD$_{D2-D5}$, respectively) and calculate the sensitivity and specificity of the DT model.

Feature Importance

For a variable Xj, it was computed as the sum of the weighted impurity reduction p(t)Δi(t) for all nodes t where Xj is used, averaged over all trees φm (for m=1, . . . ,M):

$$Imp(X_j) = \frac{1}{M}\sum_{m=1}^{M}\sum_{t\in\varphi_m} 1(j_t = j)[p(t)\Delta i(t)],$$

where M=100, p(t) is the proportion N_t/N of samples reaching t, jt denotes the identifier of the variable used at node t, and Δi(t) is the impurity reduction at node t:

$$\Delta i(t) = i(t) - \frac{N_{t_L}}{N_t}i(t_L) - \frac{N_{t_r}}{N_t}i(t_R)$$

Python Code

The Jupyter notebook file "Decision Tree analysis for MOD—Cross validation_final.ipynb" contains the Python code for CART analysis and feature importance calculation.

Statistical Analysis

All data are presented as median (interquartile range) or mean±SD. Statistical comparisons were performed using Mann-Whitney U-Test (for continuous data) or Fisher's exact test (for categorical data), as appropriate. Group-time interactions of plasma inflammatory mediators' levels were determined by One- or Two-Way Analysis of Variance (ANOVA), as appropriate. To quantify the dynamic production of the statistically significant mediators, we calculated the AUC using the mean values for each time point in a given time frame, and then calculated the fold change difference between the study groups. P<0.05 was considered statistically significant for all analyses.

Results

Defining a Threshold for a MODS-Based Primary Outcome

MODS correlates with quantifiable clinical and inflammation variables and also adverse in-hospital outcomes, such as nosocomial infection (NI); therefore was used as the primary outcome for the identification of prognostic variables. Because MOD typically peaks within the first 5 days after injury, we identified the Marshall MOD score metrics from days (D) 2-5 with the highest correlation with NI rates. Shown in FIG. 3 are the 5 MOD score metrics (out of 16 tested) that had the highest correlation with NI rates. Metrics that averaged MOD score across a combination of days between days 2-5 correlated the best with MOD score averaged across days 2-5 (aMOD$_{D2-D5}$) as the highest ranked. These metrics were also among the highest for correlating with ICU and total length of stay (FIG. 3). Decision List analysis was performed on the top-ranked metrics to define the MOD score cut-off values that segregated the greatest number of patients with the highest incidence of NI (FIG. 4). This identified a MOD score threshold of three for aMOD$_{D2-D5}$. Therefore, aMOD$_{D2-D5}$ of >3 was used to segregate High from Low MOD score patients.

The High aMOD$_{D2-D5}$ group (n=72) was comprised of 19% of the total derivation cohort and exhibited no significant difference in age or sex distribution compared to the Low aMOD$_{D2-D5}$ group (n=304). In addition, the High aMOD$_{D2-D5}$ group experienced a greater magnitude of injury (higher ISS), a lower GCS, and a higher transfusion requirement. As predicted, the incidence of adverse in-hospital outcomes including ICU and total hospital LOS, days on mechanical ventilation, and NI rates were significantly higher (P<0.001 for each) in the High aMOD$_{D2-D5}$ group when compared to the Low aMOD$_{D2-D5}$ group. The abbreviated injury scale revealed statistically significant differences in the head and extremity regions (P<0.001) in the High aMOD$_{D2-D5}$ group. However, we note that quantitative data on the extent of injuries are not typically obtained upon admission, and are therefore not available for early stratification.

The High vs. Low aMOD$_{D2-D5}$ Cohorts Differ in Patterns and Levels of Inflammatory Mediators Eleven inflammation biomarkers (out of 30 measured) were significantly different in the High aMOD$_{D2-D5}$ group vs. the Low aMOD$_D$2-D5 group upon admission. Of these, IL-6, MCP-1/CCL2, IL-10, and IL-8/CCL8 were the most significantly different, being all higher in the High aMOD$_{D2-D5}$ group when compared to the Low aMOD$_{D2-D5}$ group (P<0.001). In comparing the AUC for the biomarkers over two time intervals, 0-24 h and 2-5 days, we observed significant differences for many of the 30 biomarkers in the High compared to the Low aMOD$_{D2-D5}$ groups. This analysis confirmed that the High aMOD$_{D2-D5}$ group had markedly different levels of inflammatory mediators in the plasma both at admission and over time. In addition, DyNA demonstrated divergent dynamic networks of systemic inflammation in the High vs. Low aMOD$_{D2-D5}$.

Admission Clinical and Biomarker Data Predict Patient MOD Score Categories

We next established statistical methods to identify the clinical and inflammation biomarker variables obtained upon admission that exhibit the highest sensitivity for the prediction of High aMOD$_{D2-D5}$. The goal of this analysis was to develop methods to test the premise that data gathered in the "diagnostic" window could be useful to stratify patients. Because we restricted the data to admission variables (clinical data and first blood draw analysis), we refer to this scenario as "a narrow (e.g., short-time frame) diagnostic window" scheme. For many of the parameters measured at admission, the data distribution was found to not be normal and lognormal transformations did not appear fully adequate. We therefore, hypothesized that a model that classified based on ranks would perform with higher sensitivity than models designed for normally distributed data.

Using inflammation biomarkers alone, the highest Spearman correlations between admission biomarker levels and non-binary aMOD$_{D2-D5}$ identified IL-6 (correlation coefficient [CC]=0.31), IL-10 (CC=0.31), MCP-1/CCL2 (CC=0.46), and IL-8/CCL8 (CC=0.35) as the best predictors of High aMOD$_{D2-D5}$. Classification models of the separating hyperplane type based on ranks identified threshold values of IL-6=120.9 pg/mL, IL-10=62.8 pg/mL, MCP-1/CCL2=787 pg/mL, and IL-8/CCL8=38.1 pg/mL. An internal cross-validation on these four biomarkers suggested that the combination of MCP-1/CCL2, IL-6, and IL-10 alone yielded the highest sensitivity, allowing us to use IL-8/CCL8 as a 'tiebreaker' to correctly classify patients. This process was repeated 5000 times. The results were stable and demonstrated the probability of correctly classifying the High aMOD$_{D2-D5}$ patients at 76% (sensitivity) and Low aMOD$_{D2-D5}$ patients at 70% (specificity).

We then carried out the same analysis on 25 routine admission clinical variables (FIG. 5). This analysis yielded chloride (Cl), carbon dioxide ($CO_2$), creatinine, PTT, platelet counts (count X $10^3$/µL), monocyte counts (percentages in the WBC differential), and shock index as the clinical variables that correlated best with the aMOD$_{D2-D5}$ score. Regressions on ranks (128 in total) suggested that the optimal predictive combination consisted of CI, creatinine, and PTT. A patient with rank sum higher than 559 was predicted to develop an aMOD$_{D2-D5}$ MOD score reading>3, otherwise the patient would be predicted to have an aMOD$_{D2-D5}$<3. This model correctly classified 75% of the patients that developed High aMOD$_{D2-D5}$ (sensitivity) and 64% of patients that had Low aMOD$_{D2-D5}$ (specificity).

Figure 6:
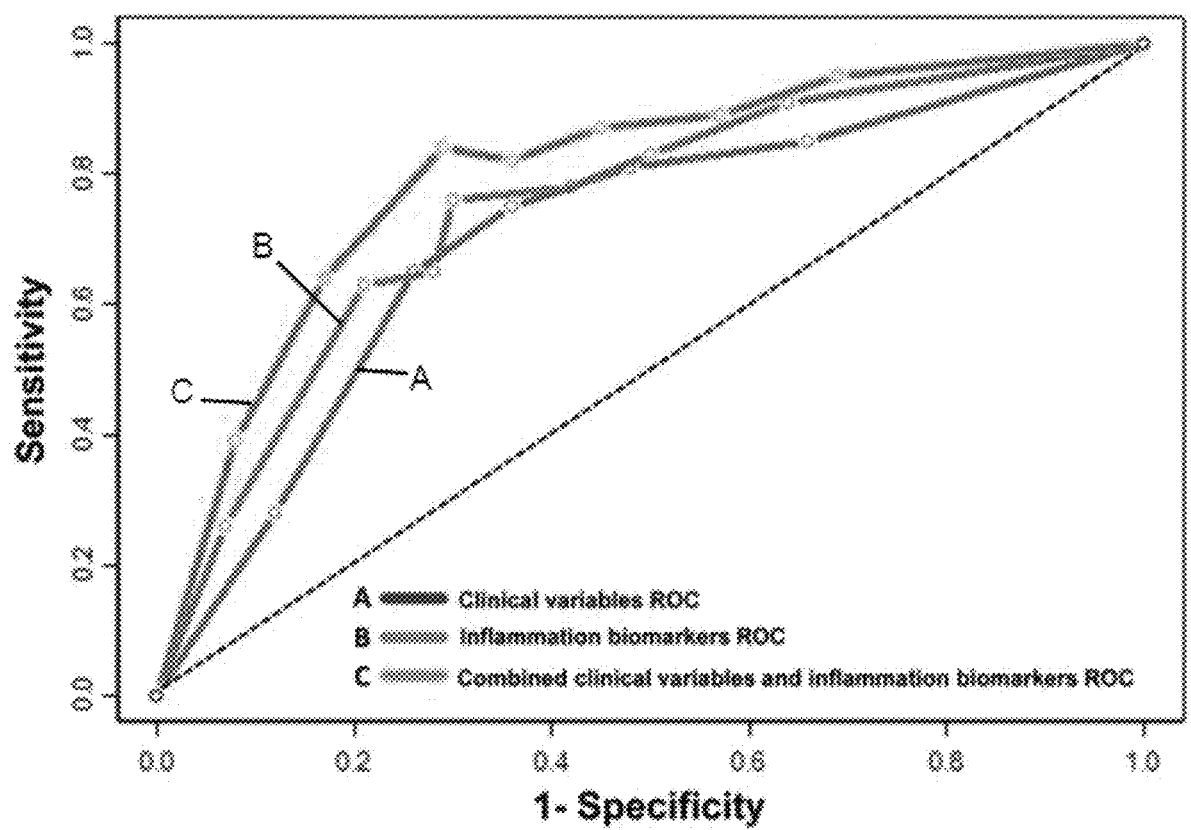
FIG. 6 shows receiver operating characteristic (ROC) curve for the three prognostic models derived using data from the derivation cohort. (A) ROC curve for model based on admission clinical variables (sensitivity=75% and specificity=64%), area under the curve (AUC)=0.72 (95% confidence interval [CI]=0.65–0.79). (B) ROC curve for the inflammation biomarker specific-predictive model (sensitivity=76% and specificity=70%), AUC=0.78 (95% CI=0.72–0.84). (C) ROC curve for the model based on the combination of admission clinical variables and inflammation biomarkers (sensitivity=84% and specificity=71%), AUC=0.82 (95% CI=0.76–0.87).
Figure 7:
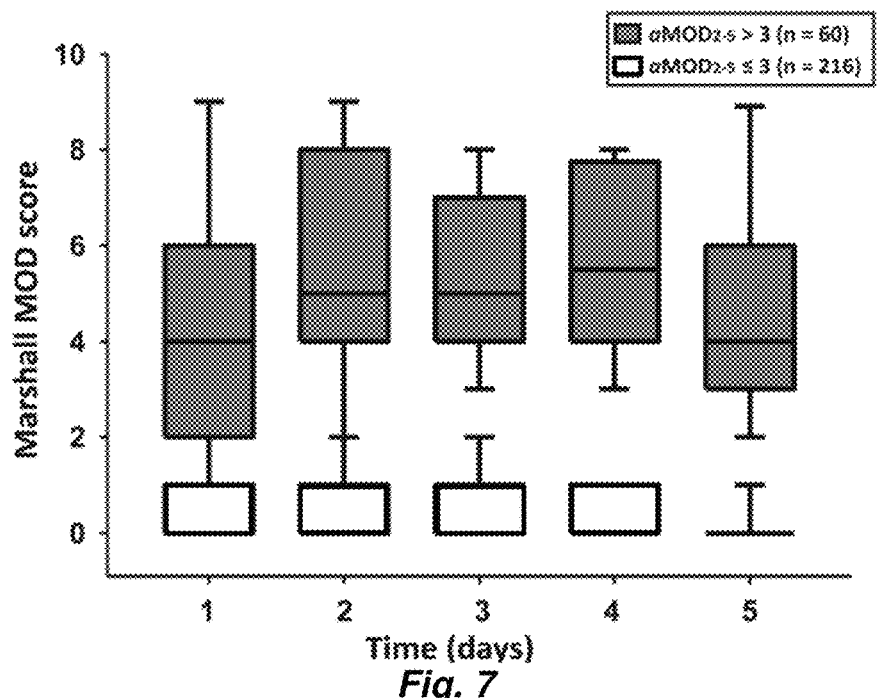
FIG. 7 shows the average MOD score days 2-5 (aMOD$_{D2-D5}$) trajectories of the correctly classified patients (either High or Low aMOD$_{D2-D5}$) derived from the predictive combined admission biomarker and clinical variables model. Data presented as median (interquartile range). The aMOD$_{D2-D5}$>3 group (n=60) had a statistically significantly higher degree of organ dysfunction that persisted from days 1 to 5 post-injury compared to the aMOD$_{D2-D5}$≤3 (n=216) group by Two-way ANOVA.

Next, we sought to establish a model that combined inflammation biomarkers and clinical variables. Initially we used Lasso Sparse Logistic modeling on 5 folds (80% training) and 100 repetitions using ranks on both inflammation biomarkers and clinical variables. Highly correlated covariates were then eliminated, and Wilcoxon rank tests on the remaining significant predictors with the binary aMOD$_{D2-D5}$ data yielded the following 10 predictor variables: IL-10, MCP-1/CCL2, IL-6, Cl, $CO_2$, creatinine, PTT, platelet counts, mono3cyte percentages, and shock index. To further identify the best subset from the ten remaining variables, we performed 1024 sparse regression choices (by either including a variable with beta=1 or excluding it with beta=0); the final model thus emerged. This model included IL-10 (interleukin 10), MCP-1/CCL2 (monocyte chemoattractant protein 1 (MCP1) and chemokine (C—C motif) ligand 2 (CCL2)), Cl, $CO_2$, creatinine, partial thromboplastin time (PTT), and platelet counts with a rank sum threshold cutoff of 1341. The sensitivity and specificity of the model were 84% and 71%, respectively. The receiver operating characteristic curves for the three stratification analyses are shown in FIG. 6, and confirm that the inclusion of both clinical and inflammation biomarker variables yields the best correlations with the MOD score outcome threshold. The dynamic MOD score trajectories of the correctly classified patients is presented in FIG. 7.

To perform an internal validation, we applied the combined clinical and biomarkers model to the 117 excluded patients of whom 98 were trauma survivors discharged from the ICU prior to day 5 and 19 patients who died while in the hospital. We used the 61% percent cutoff (rank sum of 1341) from the 376 rank-based model and applied it to this set of patients. Out of the 19 non-survivors, 15 were correctly predicted by the model to have High aMOD$_{2-5}$, thus 15/19=79% which could be interpreted as the sensitivity of the model in this case. For the survivors, 70/98=71% were correctly classified; this can be interpreted as a specificity of 71%.

To identify the impact of each individual variable on the model, we excluded the variables one at a time and re-ran the calculations. Exclusion of any single variable slightly reduced the sensitivity and specificity of the prediction model, with MCP-1/CCL2, creatinine, and IL-10 exerting the greatest influence.

We next asked how the prognostic biomarkers identified for High aMOD$_{D2-D5}$ performed when using NI as the primary outcome in place of the MOD score metric. The combined clinical and inflammation biomarkers had a sensitivity and specificity of 61% and 56%, respectively for predicting NI. Thus, the predictive sensitivity for NI was approximately the same as the percentage of High aMOD$_{D2-D5}$ patients that developed NI. These observations indicate that the variables and their thresholds are likely to be different even for related outcomes. To further examine this possibility, we identified the "best" prognostic variables for the binary outcome of NI from the admission clinical and inflammation biomarkers and found that threshold levels of MCP-1 and creatinine yielded a sensitivity of 70% and specificity of 65% for NI. These observations indicate that the optimal prognostic variables are likely to vary based on the primary outcome chosen for any given trial.

Finally, we sought to compare the performance of the combined predictive model based on ranks to other existing commonly used models. For this comparison, we chose the LASSO sparse logistic regression and decision trees models. For the LASSO, using all biomarkers and clinical variables with complete data, the data were first log-transformed by t=log(1+y) and standardized, where y are the original responses, to yield log-responses that could be considered Gaussian. A 5-fold cross-validation over 100 iterations/seeds was used to randomly select data samples that comprise the training and test sets. For each iteration/seed, a LASSO sparse logistic regression model using an L1 penalty was run on the training data. The predicted beta coefficients for the test fold were then found and all coefficients were obtained after iterating over every fold. For each iteration, we obtained a matrix of beta coefficients for each variable at each fold. If a coefficient returned by LASSO was nonzero, we replace it with a count of 1. We averaged the number of times (across iterations) that a variable was selected when training a model for each of the five folds to obtain a plot of the most frequently occurring variables. The relevant variables that emerge were consistent with those used in our models based on ranks; the models we developed simply suppress certain covariates that are highly correlated. An ROC curve was obtained that yielded an average area under the curve of 0.74 with sensitivity of 72% and specificity of 68%.

The CART (Classification and Regression Trees) decision tree analysis was preformed using the Python 2.7 Scikit-learn library. The Gini index was applied to measure the degree of impurity and the quality of a split. Given the imbalance of the sample size between the two groups (226:57 in the Low vs High aMOD$_{D2-D5}$, respectively), we sought to use a balanced set of 57:57 ratio with randomly selected 80% of the data for training and the remaining 20% of the data for testing (the ratio of sample size between the Low and High aMOD$_{D2-D5}$ groups is also balanced for both training and testing data). The models that were trained on 100 training datasets yielded an average sensitivity of 63% with standard deviation of 0.12 and an average specificity of 63% with standard deviation of 0.14 on the corresponding testing datasets. We adopted a metric known as Gini importance (Breiman, L. 2001. Random Forests. Machine learning 2001(45):5-32) for the evaluation of the feature importance for random forest model to calculate the importance of variables for predicting aMOD$_{D2-D5}$ in the trees developed on these 100 training datasets. For a variable $X_j$, it was computed as the sum of the weighted impurity reduction for all nodes t where $X_j$ is used, averaged over all trees φm (for m=1, . . . , M) where M=100. The top three important features are MCP-1 (0.107), IL-10 (0.037), and PTT (0.023) and these variables were also present among the 7 predictive variables in the combined model based on ranks. Thus, the model based on ranks provided the highest sensitivity and specificity for the incorporation of inflammatory biomarker and clinical data for the prognostication of our High aMOD$_{D2-D5}$ outcome.

Validation of the Stratification Strategy Using a Contemporary and Separate Patient Data Set To validate the optimal predictive model described above, we carried out a separate prospective study on 65 blunt trauma patients at another, comparable institution. Because PTT was not routinely measured at this institution, this variable was excluded from the analysis. Omitting PTT from the model decreased the sensitivity to 81% with a specificity of 70% using the derivation training dataset. When applied to the validation data set, the modified prediction model yielded a sensitivity of 74% (14 out of 19 High aMOD$_{D2-D5}$ patients classified correctly) and specificity of 80% (41 of 51 Low aMOD$_{D2-D5}$ patient classified correctly). Thus, the model performed well when adapted to a contemporary and prospectively gathered data set from a separate institution.

In conclusion, in the current study, we set forth an operational construct based on time windows for the design of early interventional trials in trauma patients that incorporates stratification. After identifying a MODS score threshold to serve as a primary endpoint, we established the statistical methods to identify the variables, obtained at admission, that had the highest sensitivity for prognosticating for the MOD score metric. The methods were then validated using an excluded data set from one institution and a prospectively gathered trauma patient data set from a separate institution.

The time-window model lends itself to customization. For example, widening the time frame of the initial diagnostic window would permit the inclusion of additional stratification data, such as dynamic changes in clinical parameters, biomarkers or cell based assays (e.g., genotyping) and information on interventions. It is likely that this would increase the accuracy of stratification and, if the expression of the biological drug target persisted, allow for even more precision in patient- and target-specific interventional trials. However, widening the diagnostic window would come at the cost of delaying the onset of the interventional window. All the parameters identified as useful for stratification in our studies can be measured with existing assays in the first 1-2 hours after the initial blood draw, and fit the "narrow or short diagnostic window" model. It is anticipated that the model could be adapted to almost any meaningful primary outcome. However, as shown by our analysis of NI as an outcome, the prognostic variables and their thresholds are likely to be outcome-dependent.

One of our goals was to develop the mathematical and statistical methods needed to combine data with both normal and non-normal distributions to identify prognostic variables for early patient stratification. This is important because many potentially useful variables (e.g., inflammation biomarker levels) exhibit wide and non-normal distributions in trauma patients. Therefore, in this modeling exercise, we included 25 routine clinical variables and 30 inflammation biomarkers in the model development. Indeed, our method using ranks for variable identification outperformed traditional models for stratification including LASSO Sparse Logistic as well as decision trees models. Thus, our results suggest that future work on the identification of prognostic variables should include a comparison of methods and incorporate methods based on ranks.

Although this is the first study to incorporate both clinical variables and inflammation biomarkers into a predictive model, there are many other variables that could be included in an optimized model. For example, the Denver group found that age, intubation, hematocrit, systolic BP, blood urea nitrogen, and white blood cell count obtained at admission could be used to develop a score for clinical decision support that predicted a SOFA threshold in trauma patients on day 7 (Vogel J A, et al. Prediction of postinjury multiple-organ failure in the emergency department: development of the Denver Emergency Department Trauma Organ Failure score. *J Trauma Acute Care Surg* 2014; 76(1):140-145.). The model and methods developed here could incorporate a wide number of potentially useful variables and we propose to include additional novel biomarkers, genetic markers and the full range of available clinical data in future iterations of the model.

The analysis of inflammation biomarker patterns shown in this study reveals major differences in the levels and patterns of specific mediators upon presentation and over time between the High and Low $aMOD_{D2\text{-}D5}$ groups. Some of this may be driven by the nature and magnitude of the injuries suffered by the patients. However, we have shown that even when matching for injury severity, patients that go on to develop complications such as NI and higher degrees of MOD have distinct inflammation biomarker patterns in the first 24 h. It noted that the Low $aMOD_{D2\text{-}D5}$ group exhibited a much more coordinated immune network upon presentation based on Dynamic Network Analysis than the High $aMOD_{D2\text{-}D5}$ patients, despite higher levels of many of the inflammation biomarkers in the High $aMOD_{D2\text{-}D5}$ group through the first five days. The level of coordination could relate to levels of the mediators in addition to the dynamic changes within time intervals. For example, the relatively limited variability and low levels in the Low $aMOD_{D2\text{-}D5}$ group could partially explain the initial high level of coordination observed in this group. The same analysis showed that inflammatory networks dissipate rapidly in the Low $aMOD_{D2\text{-}D5}$ patients, and it is this group that had a low incidence of in-hospital complications. In contrast, the High $aMOD_{D2\text{-}D5}$ patients exhibited the formation of persistent, but loosely connected inflammatory networks over time, raising the possibility that inflammation persisted, but in a poorly coordinated and dysfunctional manner.

Example 2—Snp Analysis

In Schmunek et al. (An Enrichment Strategy Yields Seven Novel Single Nucleotide Polymorphisms Associated with Mortality and Altered Th17 Responses Following Blunt Trauma. Shock, Vol. 49, No. 3, pp. 259-268, 2018), seven single nucleotide polymorphisms (SNPs) were identified as being associated with an altered Th17 response and mortality after moderate to severe blunt trauma. The table provided in FIG. 8 identifies each SNP. Further details regarding each SNP is provided in the National Center for Biotechnology Information (NCBI) SNP database, dbSNP. Three of the risk alleles were homozygous (AA), while four were heterozygous (AB). The risk allele for each SNP at the position identified in FIG. 8 is as follows: rs10741668-C; rs10790334-G; rs2065418-C; rs2241777-G; rs3134287-T; rs3098223-A; and rs906790-T.

The following investigates a novel single nucleotide polymorphism (SNP) associated with altered inflammation and adverse clinical outcomes in severe blunt trauma. Patients with the MPPED2 rs2065418 AA SNP exhibited longer hospital and intensive care unit stays, higher multiple organ dysfunction scores, greater requirement for mechanical ventilation, elevated plasma creatinine levels, and unique dynamic networks of systemic inflammation. MPPED2 rs2065418 AA SNP therefore provides a novel diagnostic marker for stratifying severely injured patients and provide mechanistic insights into the genetic susceptibility to organ dysfunction after severe injury.

Materials and Methods

Patients 384 blunt trauma survivors were enrolled for initial screening, after admission to the emergency department of the UPMC Presbyterian hospital (a Level 1 trauma center). DNA samples were obtained upon admission to the trauma bay. Clinical and biochemical data were collected from the electronic medical records. The primary focus of this study was on the association of potential SNPs following severe injury. Accordingly, we focused on 84 severely injured blunt trauma survivors (ISS≥25; mean age: 41.6±2 years [min: 18 y; max: 83 y]; mean ISS: 34.5±0.8 [min: 25; max: 54]; 23 females, 61 males).

DNA Sampling and Single-Nucleotide Polymorphism Genotyping

DNA was prepared from whole blood samples and analyzed using Illumina® arrays. To validate the Illumina-derived MPPED2 genotype, real-time polymerase chain reaction (PCR) was carried out.

Whole blood samples were collected into heparinized tubes. DNA was extracted using the QIAamp® DNA Blood Midi Kit (QIAGEN, Valencia, CA) as per manufacturer's specifications. Single nucleotide polymorphism genotyping was performed with 200 ng of genomic DNA input using the Human Core Exome-24 v1.1 BeadChip (Illumina, San Diego, CA) following the manufacturer's Infinium® HTS Assay protocol. Briefly, DNA was denatured in 0.1 N NaOH and neutralized prior to isothermal amplification. Amplified DNA was fragmented and then hybridized to locus-specific 50mers that make up the array for 16-24 h with rocking at 48° C. After removal of unbound or non-specifically annealed DNA, single base extension of the 50mer oligonucleotides was performed with labeled nucleotides, which were scanned using an Illumina iScan with autoloader 2.x. Data analysis was performed using Illumina Genome Studio 2.0.

Real-time PCR was carried out in 96-well FG-Microplates using Applied Biosystems kits (TaqMan SNP genotyping assay and TaqPath ProAmp master mixes, Waltham, MA). The reactions were carried out using 20 ng of human genomic DNA in a total volume of 20 μl. PCR involved standard cycles including an initial 95° C. for 12 min and 40 cycles of denaturation at 95° C. for 15 sec, and annealing/extension at 60° C. for 1 min using a 7900HT Fast Real-Time PCR system (Applied Biosystems, Waltham, MA). Endpoint reads were done on the plates. Results were analyzed using the Applied Biosystems Software version SDS2.4.

Analysis of Linkage Disequilibrium

Linkage disequilibrium (LD) is defined as alleles from two nearby genetic variants that commonly occur together in a non-random, linked fashion. LD is only possible, if the two alleles are in neighboring location on the same chromosome. Accordingly, we tested the previously discovered set of seven SNPs for LD using online analysis tools provided by NIH, LDmatrix for graphics and LDpair for statistics. Results are based on all populations of the Phase 3 of the 1000 Genomes Project and given in both D' and $R^2$.

In further detail, linkage disequilibrium of two alleles refers to one defined population and can be quantified by its coefficient D. D is calculated by the following formula: $D_{AB}=p_{AB}-p_A p_B$, $p_A$ being the frequency for allele A, $p_B$ being the frequency for allele B and $p_{AB}$ being the frequency the two alleles A and B occurring together. The alleles A and B are in linkage disequilibrium, if $D_{AB} \neq 0$. $D_{AB} > 0$ means positive linkage, $D_{AB} < 0$ means negative linkage. If $D_{AB}=0$, no linkage between the two alleles exists and they are said to be in linkage equilibrium.

D varies with different frequencies and is therefore mostly not comparable. Accordingly, D', the normalized form of D is used to display the relation between two alleles. The possible values range from 0-1 with higher values indicating a stronger linkage of the two alleles.

Alternatively, the correlation coefficient R or its square $R^2$ can be used to describe the linkage. R is calculated as follows: $D/\sqrt{p_A(1-p_A)p_B(1-p_B)}$. The possible values also range from 0-1 with higher values indicating a stronger correlation of the two alleles A and B.

Serial Analysis of Inflammatory Mediators

Plasma levels of the following 31 inflammatory mediators were analyzed: Eotaxin, GM-CSF, IFN-α, IFN-γ, IL-1β, IL-1RA, IL-2, sIL-2Rα, IL-4, IL-5, IL-6, IL-7, IL-8, IL-9, IL-10, IL-13, IL-15, IL-17A, IL-17E/25, IL-21, IL-22, IL-23, IL-33, IP-10, MCP-1, MIG, MIP-1α, MIP-1β, $NO_2^-/NO_3^-$, soluble ST2 (sST2), and TNF-α. Whole blood samples were withdrawn in heparinized tubes 3 times in the first 24 h after admission, and then daily for 7 days. The samples were kept on ice and centrifuged to obtain plasma, and then stored at −80° C. until assayed for inflammatory mediators. The Luminex™ 100 IS analyzer (Luminex, Austin, TX) and Human Cytokine/Chemokine MILLIPLEX™ Panel kit (Millipore Corporation, Billerica, MA) were used to measure plasma levels of Eotaxin (CCL11), interleukin (IL)-1β, IL-1 receptor antagonist (IL-1RA), IL-2, soluble IL-2 receptor-α (sIL-2Rα), IL-4, IL-5, IL-6, IL-7, IL-8 (CCL8), IL-10, IL-13, IL-15, IL-17A, interferon (IFN)-α, IFN-γ, IFN-γ inducible protein (IP)-10 (CXCL10), monokine induced by gamma interferon (MIG; CXCL9), macrophage inflammatory protein (MIP)-1α (CCL3), MIP-1β (CCL4), monocyte chemotactic protein (MCP)-1 (CCL2), granulocyte-macrophage colony stimulating factor (GM-CSF), and tumor necrosis factor alpha (TNF-α). Human Th17 MILLIPLEX™ Panel kit (Millipore Corporation, Billerica, MA) was used to measure IL-9, IL-21, IL-22, IL-23, IL-17E/25, and IL-33. Nitrite/Nitrate ($NO_2^-/NO_3^-$) levels were measured by a Griess Reagent colorimetric assay (Cayman Chemical, Ann Arbor, MI). Plasma levels of soluble ST2 (sST2) were measured by a sandwich ELISA assay (R&D Systems, Minneapolis, MN). All cytokine/chemokine mediator concentrations are given in pg/ml; $NO_2^-/NO_3^-$ concentrations are in μM. Experimental data are shown as mean±SEM.

Statistical Analyses

All analyses were carried out using GraphPad Prism 7 (Graphpad Software, Inc., San Diego, CA). A p-value of less than 0.05 was considered significant for all analysis. D'Agostino & Pearson normality test were used to identify if the patient demographics and outcomes were distributed normally. Student's-t test was used to compare differences between groups of patients with regard to normally distributed demographics and outcomes. The Mann-Whitney U test was used to compare differences between groups of patients with regard to non-normally distributed patient demographics and outcomes. One-Way ANOVA was used for multiple group comparisons regarding normally distributed data, followed by Tukey's multiple comparisons post hoc test. Multiple group comparisons of non-normally distributed data were performed using Kruskal-Wallis test, followed by Dunn's multiple comparisons post hoc test. Fisher's Exact test was used to compare patient demographics and outcomes organized in contingency tables. Two-Way ANOVA was used to determine time-dependent changes of plasma creatinine levels, MODScores, and circulating inflammatory mediators as a function of patient sub-group.

Dynamic Network Analysis

Dynamic Network Analysis (DyNA), carried out in Matlab® software, was used to define the central inflammatory network mediators as a function of both time and patient sub-group. Network complexity scores (NCS) were calculated and presented as trajectories. Heat maps were created to show the connectivity of the different inflammatory mediators over time.

Figure 9A:
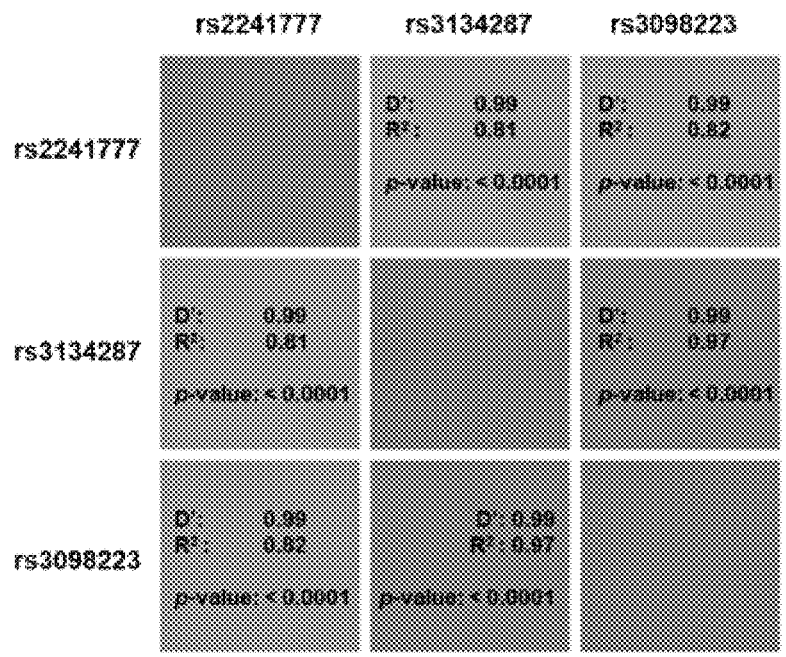
FIGS. 9A and 9B show testing for linkage disequilibrium shows strong correlations between rs2241777, rs3098223 and rs3134287, all located on chromosome 8. The SNPs located on chromosome 8 (rs2241777, rs3098223 and rs3134287) showed strong linkages between each other (D'=0.99, p-value<0.0001 for all comparisons) (FIG. 9A), while the three SNPs on chromosome 11 (rs2065418, rs10741668 and rs10790334) showed no linkage (FIG. 9B).
Figure 9B:
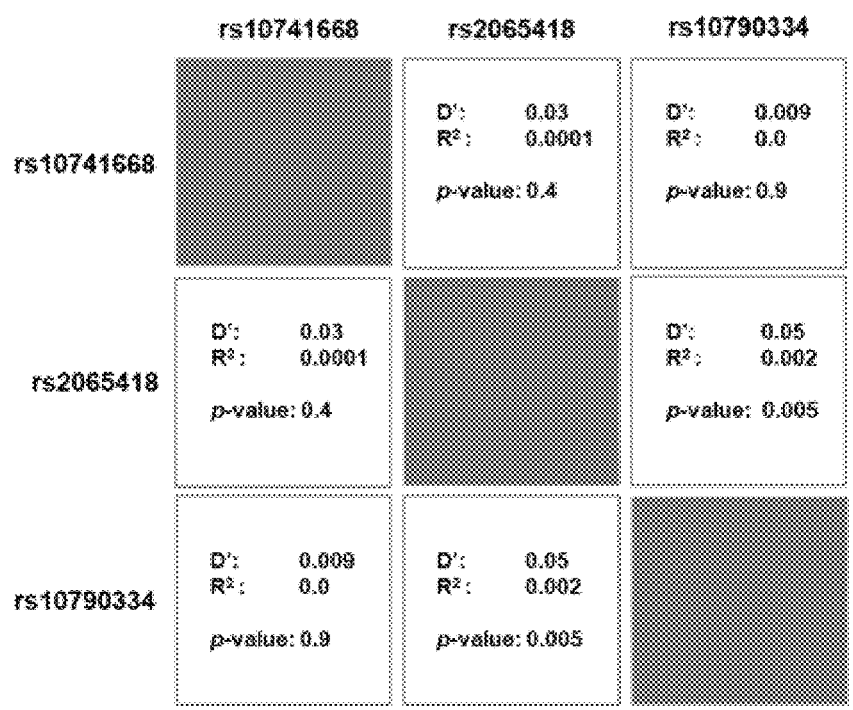

In further detail, using inflammatory mediator measurements of at least three time-points for experimental group, networks were created at nine consecutive time periods (0-12 h, 12-16 h, 16-24 h, Day 2, Day 3, Day 4, Day 5, Day 6, and Day 7) using Matlab® software. Connections ([network edges] represent trajectories of inflammatory mediators [network nodes] that move in parallel; positive: same direction; negative: opposite direction) were created if the Pearson correlation coefficient between any two nodes (inflammatory mediators) at the same time-interval was greater or equal to a threshold of 0.85, as indicated. The network complexity for each time-interval was calculated using the following formula: Sum $(N1+N2+\ldots+N_n)/n-1$, where N represents the number of connections for each mediator and n is the total number of mediators analyzed. The total number of connections represents the sum of the number of connections across all time intervals for all patients in a given sub-group. In previous studies, we showed that rising network complexity is associated with rising MODScores when comparing trauma survivors vs non-survivors Results Analysis of Individual SNPs Associated with Trauma Non-Survivors We first sought to determine if any of the SNPs we associated previously with trauma non-survivors was, on its own, associated with adverse outcomes in trauma survivors. Of the 7 non-survivor-associated SNP genotypes, only 4 (rs906790, rs2065418, rs10790334, and rs10741668) could be assessed individually due to linkage disequilibrium in the remaining 3 SNPs (rs2241777, rs3134287, and rs3098223, FIGS. 9A and 9B). Accordingly, we created single-SNP groups for the 4 non-linked SNPs (and excluding the other 3 SNPs) from our cohort of 384 blunt trauma survivors. This resulted in the following 4 groups: rs906790 AB only (n=20 patients), rs2065418 AA only (n=8 patients), rs10790334 AA only (n=12 patients), and rs10741668 AA only (n=22 patients). All 4 single SNP groups had comparable demographics, but only rs2065418 AA, located in the MPPED2 gene, exhibited a trend towards worse outcomes.

Severely Injured Blunt Trauma Survivors with the rs2065418 AA Genotype Have Significantly Worse Clinical Outcomes Compared to Survivors with an AB/BB Genotype Given the putative roles of MPPED2 in tissue homeostasis, as well as its association with mechanical ventilator-induced lung injury, we hypothesized that a certain injury severity threshold must be exceeded in order to observe the impact of rs2065418 AA on blunt trauma outcomes.

Accordingly, we stratified 84 severely injured blunt trauma patients (commonly defined as ISS≥25) based on their rs2065418 genotype. The resultant two groups were as follows: 1) rs2065418 AA group (n=35; age: 42.5±3.1 yr [min: 18 yr; max: 83 yr]; ISS: 36±1.5 [min: 25; max: 54]; gender: 12 females, 23 males); and 2) rs2065418 AB/BB control group (n=49; age: 41±2.6 yr [min: 18 yr; max: 82 yr]; ISS: 33.5±0.9 [min: 25; max: 47]; gender: 11 females, 38 males) (FIG. 10). Furthermore, the groups were similar in AIS distribution and comorbidities (data not shown). We confirmed that these patients carried the correct rs2065418 genotype using real-time PCR (data not shown).

Figure 11:
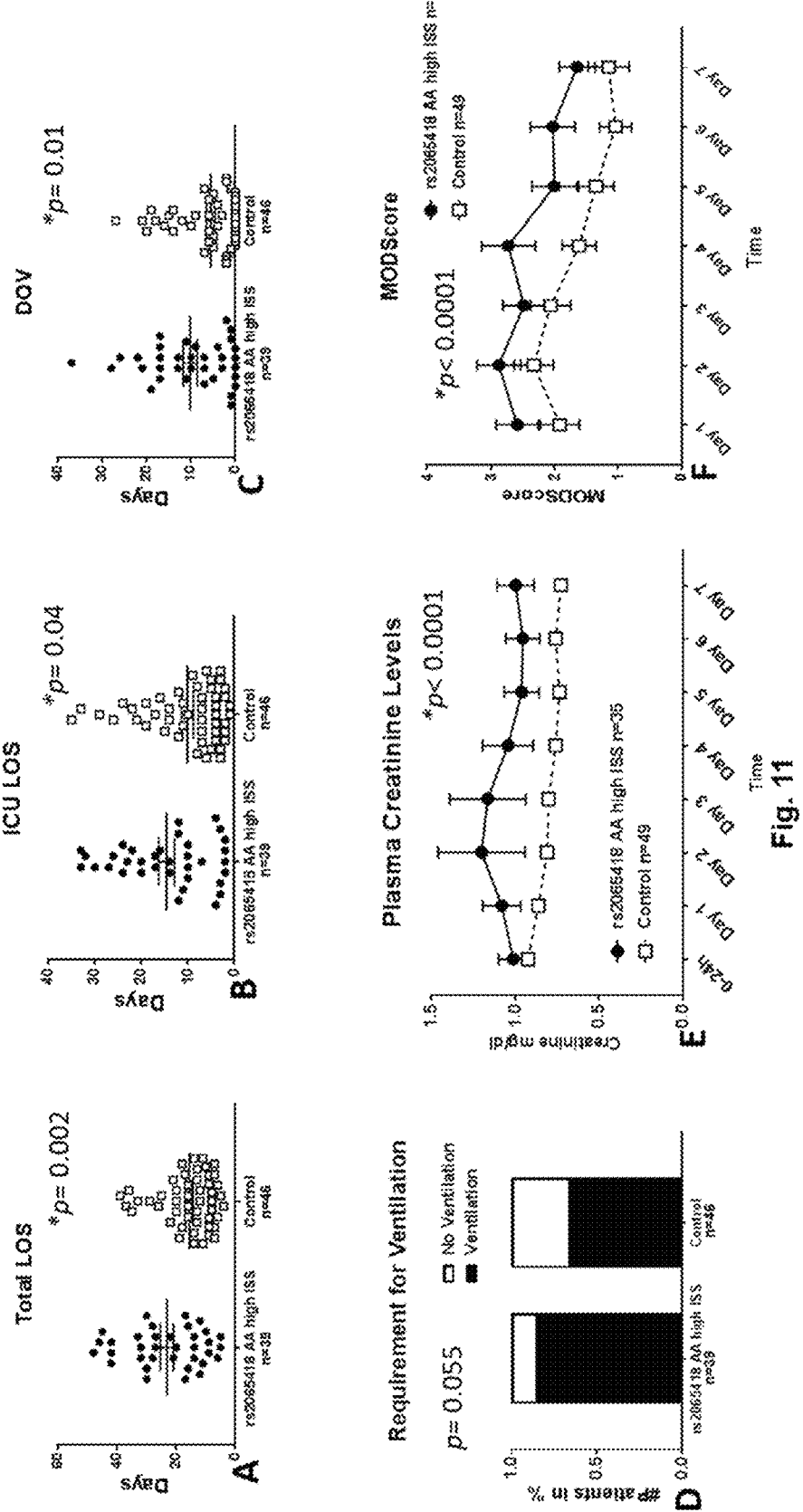
FIG. 11 provides graphs showing that severely injured rs2065418 AA patients exhibit worse clinical outcomes vs. severely injured rs2065418 AB/BB controls. High severity rs2065418 AA patients and control rs2065418 AB/BB patients were assessed for clinical outcomes as described in the Materials and Methods. High ISS rs2065418 AA patients exhibited longer total LOS (23±2 d vs. 16±1 d, p=0.006 [A]), longer ICU LOS (15±2 d vs. 10±1 d, p=0.04 [B]), longer DOV (10±2 d, 6±1 d, p=0.0123 [C]), elevated plasma creatinine levels (p<0.0001 [E]), and higher Marshall MOD-Score over 7 days (p=0.0001 [F]) compared to the control group of high ISS rs2065418 AB/BB patients. The requirement for ventilation was nearly statistically significant (p=0.055 [D]).

Severely injured patients carrying the rs2065418 AA genotype exhibited significantly longer hospital length of stay (total LOS; 23±2 d) and ICU LOS (15±2 d) vs. the control group of rs2065418 AB/BB patients (LOS: 16±1 d, p=0.006; ICU LOS: 10±1 d, p=0.04) (FIG. 11 [A-B]). Furthermore, high ISS rs2065418 AA patients were on mechanical ventilation significantly longer (DOV; 10±2 d vs. 6±1 d in controls; p=0.01) and had higher plasma creatinine levels over the first 7 days compared to the control group (p<0.0001) (FIG. 11 [C+E]). The rs2065418 AA patients also had higher Marshall MODScores over the first 7 days (p=0.0001) (FIG. 11 [F]). The requirement for ventilation was nearly statistically significant (p=0.055) (FIG. 11 [D]) as were the rates of nosocomial infections (57% [rs2065418 AA] vs. 38% [Control]; p=0.12). Analysis of patients carrying the AB genotype of rs2065418 vs. patients with the BB genotype did not show any significant differences in these same parameters (data not shown).

Figures 12, 13:
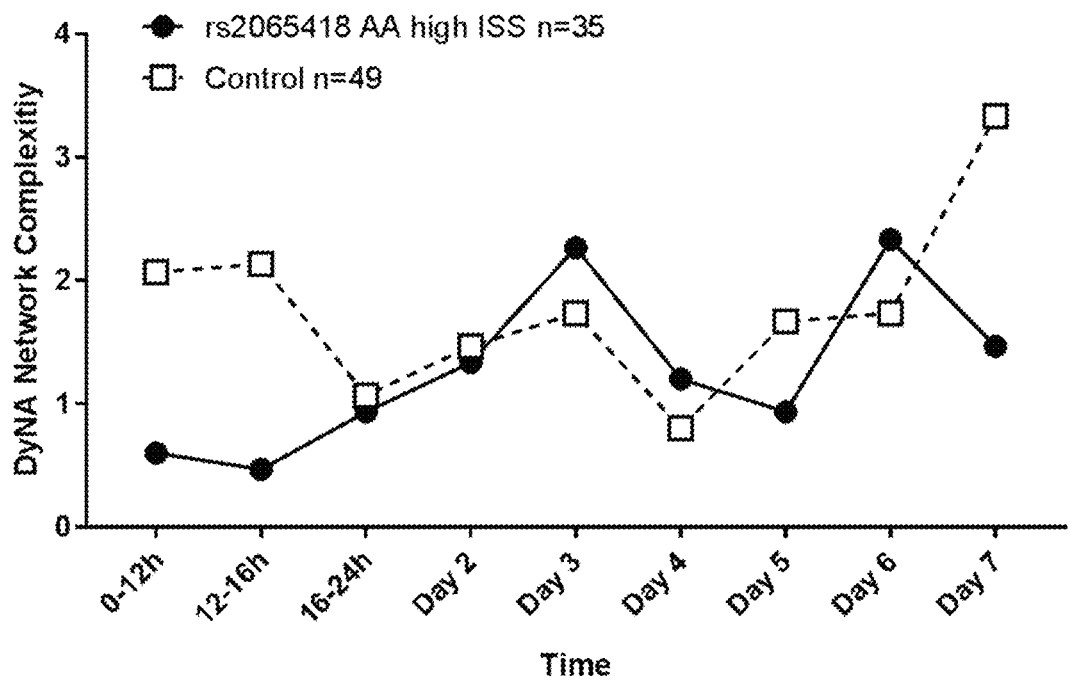
FIG. 12 is a table showing significantly different inflammatory mediators of severely injured rs2065418 AA patients vs. severely injured rs2065418 AB/BB controls.
FIG. 13. Analysis of network complexity shows an initially impaired inflammatory response in severely injured rs2065418 AA patients vs. severely injured rs2065418 AB/BB controls. DyNA of inflammatory mediators was carried out using data from admission to 7 days following injury. This analysis revealed that severely injured rs2065418 AA patients exhibit a reduced inflammatory network complexity score in the first 16 h relative to controls, before reaching levels of control AB/BB patients until day six. At day seven, control patients again exhibited an elevated complexity score compared to high ISS rs2065418 AA patients.

Severely Injured Rs2065418 AA Patients Exhibit Distinct Inflammatory Responses From Those of rs2065418 AB/BB Control Patients In our prior study, trauma survivors carrying all seven non-survivor SNPs exhibited different inflammatory responses from survivors having none of those SNPs (20). Accordingly, we next compared the dynamic changes in the circulating levels of 31 inflammatory mediators in the first seven days after injury between high ISS rs2065418 AA patients and control (high ISS AB/BB). Eleven of the 31 assessed circulating inflammatory mediators showed statistically significant differences between rs2065418 AA patients and rs2065418 AB/BB controls: rs2065418 AA patients expressed higher levels of Eotaxin (p=0.001), MCP-1 (p=0.0001), and MIG (p=0.04) vs. rs2065418 AB/BB control patients, and lower plasma levels of GM-CSF (p=0.04), IFN-α (p=0.006), IL-4 (p=0.04), IL-9 (p=0.006), IL-10 (p<0.0001), IL-15 (p=0.02), IL-17A (p=0.002), and IL-23 (p=0.03) (FIG. 12).

High ISS Rs2065418 AA Patients Show Impaired Mediator Connectivity and Network Complexity Over 7 Days Following Injury as Compared to Rs2065418 AB/BB Control Patients Rising network complexity is associated with elevated MODScores in the first five days after trauma, which is in turn associated with the set of seven SNPs that include rs2065418 AA. Accordingly, we hypothesized that severely injured patients that carry the rs2065418AA genotype and exhibit higher MODScores in the first seven days (FIG. 11 [F]) would exhibit a higher network complexity scores (NCS) than control. Contrary to our hypothesis, high ISS rs2065418 AA patients showed a reduced inflammatory network complexity in the first 16 h relative to controls (NCS: 0.6-0.5 vs. 2.1), before reaching levels of control AB/BB patients by day six (NCS: 0.9-2.3). At day seven, control patients again exhibited an elevated complexity score compared to rs2065418 AA patients (NCS: 1.5 vs. 3.3) (FIG. 13).

We next examined the network connectivity of each inflammatory mediator assessed, in order to help define dominant pathways associated with each rs2065418 genotype. The total number of connections observed in rs2065418 AA patients was 28% lower compared to rs2065418 AB/BB control patients (346 vs. 480 total connections) over a time course of seven days after admission. In the rs2065418 AA group, the most connected mediators (defined as the $3^{rd}$ quartile of total connections in their respective patient sub-groups) were GM-CSF, IL-1β, IFN-α, IL-2, IL-33, MIP-1β, IL-23, and IL-17A ($3^{rd}$ quartile: 17.5). In contrast, IL-2, IL-1β, IL-15, IL-17A, MIP-1β, MIP-1α, IFN-α, IL-33, and IFN-γ were the most connected mediators in the control group ($3^{rd}$ quartile: 25).

We next sought to define, in granular detail, the dynamic inflammatory networks associated with each rs2065418 genotype over the initial 24 h following injury. As quantified in FIG. 13, these early networks were sparser in high ISS rs2065418 AA patients vs. controls. In the initial 16 h in controls, DyNA suggested the activation of Th1, Th2, and Th17 pathways, as evidenced by networks involving the cytokines IL-2, IFN-γ, and TNF-α (Th1); IL-4, IL-5, and IL-6 (Th2); and IL-17A, IL-17E/25, IL-21, and IL-22 (Th17). Furthermore, MIP-1α and MIP-1β suggested granulocyte activation. The mediators were highly connected, which suggested a well-organized and robust inflammatory response in control patients. In contrast, the networks of the high severity rs2065418 AA patients were fragmented, which suggests a less organized and weaker initial inflammatory response in the first 16 hours. The mediators involved in these networks were less connected, but also suggested activation of Th1 (IL-2 and TNF-α), Th2 (IL-4, IL-5, and IL-13) and Th17 (IL-17A, IL-17E/25, IL-22, and IL-23) along with the activation of chemokine pathways (MIG and IP-10).

The present Example investigated an SNP in the MPPED2 gene associated with altered inflammation and adverse clinical outcomes in severe blunt trauma. Severely injured patients carrying the AA genotype of the MPPED2 SNP rs2065418 exhibited greater hospital and ICU LOS, higher MODScores over time, longer time on mechanical ventilation, elevated plasma levels of creatinine over time, and alterations in dynamic networks of systemic inflammation.

Example 3

Clinical data, including injury characteristics, biochemical and physiologic data, procedures, transfusions, and in-hospital complications were obtained from the electronic medical records from 376 trauma patients initially admitted to the ICU and that survived to discharge. A previously characterized organ failure score comprised of average MOD score across days 2-5 was subjected to Fuzzy C-means Clustering Analysis (FCM) followed by eight common Clustering Validation Indices (CVI) to derive organ dysfunction patterns among 376 trauma patients that survived to discharge. Thirty-one inflammation biomarkers were assayed (by Luminex®) in serial blood samples (3 samples within the first 24 h and then daily up to 5 days post-injury) and were analyzed using Two-Way ANOVA and Dynamic Network analysis (DyNA).

Results: The FCM followed by CVI suggested four distinct clusters based on MOD score magnitude: Cluster 1 (n=199, average MOD score=0.3); Cluster 2 (n=99, average MOD score=2); Cluster 3 (n=53, average MOD score=4); and Cluster 4 (n=25, average MOD score=7). Based on Marshall MOD score organ-specific parameters, distinct patterns of organ dysfunction were observed in each of the four clusters. There were also statistically significant differences among the four clusters with regards to in-hospital outcomes, including intensive care unit (ICU) and total hospital stay, days on mechanical ventilation, and incidence of nosocomial infection. Of the 31 biomarkers measured, IL-6, MCP-1, IL-10, IL-8, IP-10, sST2, and MIG were elevated differentially over time across the clusters. DyNA identified remarkable differences in inflammatory network interconnectivity over time among the four clusters.

Conclusion: These results suggest the existence of four distinct organ failure patterns based that can be derived from on Marshall MOD score magnitude in trauma patients following ICU admission. The organ failure patterns are preceded by distinct inflammatory responses and followed by differences in in-hospital outcomes.

Patient Enrollment, Sampling, and Data Collection

Blunt trauma patients deemed eligible for enrollment were at least 18 years of age at time of the trauma, admitted to the ICU as part of the post-trauma management, and were expected to survive beyond the initial 24 h post-injury as per the on-call trauma surgeon. Reasons for ineligibility were isolated head injury or brain death criteria, or pregnancy. Three plasma samples, starting with the initial blood draw upon arrival, were assayed within the first 24 h following injury and then from day (D) 1 to D5 post-injury. Demographic and clinical data were collected from the inpatient electronic medical record and the trauma registry database.

The Marshall Multiple Organ Dysfunction (MOD) score is a composite, standardized, and a validated metric which is calculated as index of organ dysfunction. This score includes six variables: 1) the respiratory system (PO2/FIO2 ratio); 2) the renal system (serum creatinine concentration); 3) the hepatic system (serum bilirubin concentration); 4) the hematologic system (platelet count); 5) the central nervous system (Glasgow Coma Scale); and 6) the cardiovascular system—the pressure-adjusted heart rate (PAR). Marshall MOD score was calculated on a daily basis starting from day D1 up to D5. Organ failure is known to peak within the first 5 days of injury. Therefore, out of 493 patients enrolled in the observational study, we identified a subset of patients that remained in the ICU for at least 5 days with complete MODS data for the first five days as previously described (n=376). Patients were excluded because they were discharged from the ICU prior to 5 days and therefore had incomplete MODs data (n=96) or because they died prior to discharge (n=21). The patients that died in-hospital are referenced in this study as a separate group.

Fuzzy C-Means Clustering

To identify the number of distinct MOD score-based clusters present in the first five days after injury, the average MOD scores for days 2-5 for 376 patients admitted to the ICU after trauma were subjected to fuzzy C-means (FCM) clustering. The FCM is a soft partition, unsupervised clustering method that allows each piece of data to belong to more than one cluster. The FCM assigns membership values to each of the data points that indicate the degree to which the data points belong to the different clusters. This feature, in some degree, fits the characteristic of heterogeneous clinical data that exhibits no clear boundaries between clusters. The objective function of the FCM algorithm is to minimize the algorithm (see below):

$$J(U, V) = \sum_{i=1}^{n} \sum_{j=1}^{c} (\mu_{ij})^m \|x_i - v_j\|^2$$

where $\mu_{ij} \in [0,1]$ is the membership of $x_i$ to $j^{th}$ cluster, m represents the fuzzifier parameter (set up as 2), c is the number of clusters, and $\|x_i - v_j\|$ represents the distance of $x_i$ to the center of $j^{th}$ cluster.

As described in the objective function, the number of clusters (c) needs to be preset. To define the optimal number of clusters, we performed FCM based on the Euclidean distance with c set from 2 (lowest) to 6 (highest) clusters. Next, to determine the optimal number of clusters, we utilized eight widely used Clustering Validation Indices (CVI), which allow for the quantification of intra-cluster compactness or inter-cluster separation. The CVI analysis included: C index, Dunn index, Gamma index, GDI index, G-plus index, PBM index, S-Dbw index, and Tau index. These analyses were carried out using R (The R Project for Statistical Computing, Version 3.2.2)

Analysis of Inflammation Biomarkers

Blood samples were collected into citrated tubes via central venous or arterial catheters upon admission, at least two more times in the first 24 hrs and then daily up to 7 days post-injury. The blood samples were centrifuged, and plasma was aliquoted and stored at −80° C. for subsequent analysis of inflammatory mediators (a total of 30 biomarkers). The human inflammatory MILLIPLEX™ MAP Human Cytokine/Chemokine Panel-Premixed 26 Plex, MIL- LIPLEX™ MAP Human Th17 Panel (Millipore Corporation, Billerica, MA), Luminex® 100 IS analyzer (Luminex, Austin, TX), and MAGPIX® system (Millipore-Sigma, Austin, TX) were used to measure plasma levels of interleukin (IL)-1β, IL-1 receptor antagonist (IL-1RA), IL-2, soluble IL-2 receptor-α (sIL-2Rα), IL-4, IL-5, IL-6, IL-7, IL-8 (CCL8), IL-9, IL-10, IL-13, IL-15, IL-17A, IL-17E/IL-25, IL-21, IL-22, IL-23, IL-33, interferon (IFN)-γ, IFN-α, IFN-γ inducible protein (IP)-10 (CXCL10), monokine induced by gamma interferon (MIG; CXCL9), macrophage inflammatory protein (MIP)-1α (CCL3), MIP-1β (CCL4), monocyte chemotactic protein (MCP)-1 (CCL2), granulocyte-macrophage colony stimulating factor (GM-CSF), Eotaxin (CCL11), and tumor necrosis factor alpha (TNF-α). The Luminex® system was used in accordance to manufacturer's instructions. Plasma levels of soluble ST2 (sST2) were measured by ELISA according to the manufacturers' instructions (R&D Systems, Minneapolis, MN).

Statistical Analysis

All data are expressed as mean±SEM. Statistical analysis between groups was performed by One-way Analysis of Variance (ANOVA) followed by Tukey post hoc analysis using SigmaPlot™ 11 software (Systat Software, Inc., San Jose, CA). Fisher's exact test was performed for categorical data using Graphpad PRISM (GraphPad Software, Inc., La Jolla, CA). Group-time interaction of plasma inflammatory mediators' levels was determined by Two-Way ANOVA. To quantify the overall production of the statistically significant mediators, we calculated the area under the curve (AUC) using the mean values for each time point in a given time frame, then calculating the fold change difference between groups. $P<0.05$ was considered statistically significantly different for all analyses.

Dynamic Network Analysis (DyNA)

The goal of this analysis was to gain insights into the temporal dynamic changes in network connectivity of the post-traumatic inflammatory response among the FCM-defined clusters. The mathematical formulation of this method is essentially to calculate the correlation among variables by which we can examine their dependence. To do so, inflammatory mediator networks were created in adjacent 8-h time periods for the first 24 h (0-8 h, 8-16 h, and 16-24 h) and D2-D5 (inclusive) using MATLAB™ (The MathWorks, Inc., Natick, MA). Connections in the network were created if the correlation coefficient between two nodes (inflammatory mediators) was greater or equal to a threshold of 0.8.

Results

Clustering Validation Indices Identify Four Distinct MOD Score Clusters Following Severe Injury The number of distinct severity-based MODS clusters was determined by Fuzzy C-means Clustering Analysis (FCM) using MOD scores derived from 376 severely injured trauma patients. Organ dysfunction is known to peak within the first five days after severe injury; therefore, a MODS metric based on MOD scores averaged across days 2-5 was used for this analysis. This metric correlates well with in-hospital complications such nosocomial infection rates and ICU LOS. These MOD score data were subjected to eight separate clustering validation indices to define the number of potential distinct MODS clusters. These indices, which quantify either intra-cluster compactness or inter-cluster separation, included C index, Dunn index, Gamma index, GDI index, G-plus index, PBM index, S-Dbw index, and Tau index. Six indices indicated that four clusters was the optimal number, while two indices suggested three clusters. Based on this analysis, FCM was used to segregate the patient cohort into the following four clusters: Cluster 1 (n=199, mean MOD score=0.28±0.02), Cluster 2 (n=99, mean MOD score=1.97±0.07), Cluster 3 (n=53, mean MOD score=3.99±0.12), and Cluster 4 (n=25, mean MOD score=7.13±0.23). The MOD score values on individual days as well as average scores over days 2-5 were statistically different between the four clusters as determined by Two-way ANOVA.

The Four MOD Score Clusters Differed in Injury Patterns and Presentation Characteristics In terms of overall demographics, there was no statistically significant difference in average age or male:female distribution among the four clusters. However, Cluster 1 had a statistically significantly lower average injury severity score (ISS) than Clusters 2-4 ($P_{2vs1}=0.041$; $P_{3vs1}<0.001$). There was no statistical difference in ISS between Clusters 2, 3, and 4. To determine if injury patterns differed between the clusters, the abbreviated injury scale for six body regions were compared. Cluster 2 exhibited greater rates of abdominal and extremity injuries (P=0.014 and P=0.003, respectively) when compared to Cluster 1. Patients in Cluster 3 had higher head and neck injury scores when compared to Cluster 1 and 2 (P=0.011 and 0.02, respectively) and a statistically significantly higher incidence of brain injury than Cluster 1 (P=0.003) and Cluster 2 (P=0.010). There was no difference in brain injury rates between Clusters 3 and 4. Thus, Cluster 1 patients were less severely injured while Clusters 3 and 4 included patients that were more likely to have traumatic brain injury.

We next identified the differences in physiologic and biochemical data on presentation among the four MOD score clusters. Clusters 2-4 had lower average systolic blood pressures and hemoglobin levels upon presentation when compared to patients in Cluster 1. Patients in Cluster 3 had higher blood creatinine levels on admission compared to Clusters 1 and 2. Admission coagulation parameters (Prothrombin time, International Normalized Ratio, and Partial Thromboplastin Time) were higher in Cluster 3 (16.0±0.7, P=0.007; 1.36±0.07, P=0.001; 29.0±1.2, P=0.003; respectively) and Cluster 4 (16.3±0.8, P=0.03; 1.35±0.09, P=0.037; 28.3±0.7, P=0.23; respectively) compared to Cluster 1 (14.4±0.2; 1.16±0.02; 26.3±0.3; respectively). Therefore, patients in Clusters 2-4 were more likely to be in shock at admission while patients in Clusters 3 and 4 were more likely to present with evidence of renal dysfunction and coagulation abnormalities.

MOD Score Clusters Differ in Clinical Outcomes

There were statistically significant differences among the four clusters with regards to in-hospital outcomes, including ICU and total hospital length of stay (LOS), days on mechanical ventilation as well as the incidence of nosocomial infection (NI) being all greatest in Clusters 3 and 4. Surgical intervention rates (within the first 24 h-all types of procedures) were lowest in Cluster 1 and were significantly different between Cluster 1 and Clusters 2-4. Patients in Cluster 4 were more likely to require a vascular intervention.

Patients in Clusters 2-4 were more likely to receive a transfusion in the first 24 h than patients in Cluster 1 and patients in Cluster 4 received significantly greater volumes of packed red blood cells (PRBC) and fresh frozen plasma (FFP) when compared to patients in Clusters 1-3. These findings further establish that patients that fall into Cluster 1 have less severe injuries than patients in the other clusters, while patients in Cluster 4 are distinguished by a greater need for both PRBC and FFP.

Disparate Contribution of Individual Organ Failure Components Among the Four Clusters The four clusters differed not only in the average magnitude of MOD, but also in organ failure patterns. Clusters 2-4 exhibited respiratory, cardiovascular, hematologic, and neurologic dysfunction scores that increased significantly between each severity-based cluster. Clusters 3 and 4 were distinguished from Clusters 1 and 2 by significantly more renal dysfunction. A notable increase in respiratory and cardiovascular dysfunction scores was observed in Cluster 4. Therefore, organ dysfunction becomes progressively worse across the clusters for all systems except for the hepatic component, with a notable increase in average renal dysfunction scores in Cluster 3 and marked worsening of the severity of respiratory and cardiovascular dysfunction in Cluster 4.

Distinct Inflammatory Patterns Emerge Among the Four Clusters

Seven out of the 31 biomarkers assayed exhibited statistically significant differences among the clusters upon admission and over time. These included MCP-1, IL-6, IL-10, IL-8, IP-10, sST2, and MIG. Cluster 2 was distinguished from Cluster 1 by significantly higher levels of MCP-1, IL-6, IL-10, IL-8, and sST2 early post-injury with notably sustained elevations in sST2 over 5 days. Clusters 3 and 4 exhibited further significant elevations in MCP-1, IL-6, IL-10, IL-8, and sST2 early and over time, as well as increases in IL-10 and MIG over clusters 1 and 2. The highest levels of all 7 mediators were seen in Cluster 4.

Next, we sought to define the dynamic interconnectivity among different biomarkers over time in the FCM-based MODS clusters. To do this, Dynamic Network Analysis (DyNA) was performed. This analysis identifies interconnections among mediators that exhibit dynamic changes in levels that correlate either positively or negatively. Notably, Cluster 1 exhibited a highly connected network within the first 16 h post-injury that dissipated rapidly thereafter. The networks in Cluster 2 consisted of sparsely connected networks, a pattern that persisted to day 5. In clear distinction, Cluster 3 had an increase in network connectivity over time with the greatest connectivity among mediators observed at D2-D5. Finally, Cluster 4 also exhibited a unique pattern with highly connected but uncoordinated networks throughout the 5 days. This analysis suggests that the inflammation profiles diverge early and in conjunction with the evolution of the severity and patterns of MODS following severe blunt trauma.

Characteristics of Excluded Patient Cohorts

In order to assure availability of complete MOD score data from D2-5 and complication rates through discharge, patients with incomplete MOD 2-5 data (n=96) or that died in-hospital (n=21) were not included in the initial clustering analysis. Among the 96 excluded patients, 91 were discharged from ICU prior to day 4, and their average MOD score values on days 2-4 were 0.6±0.1, 0.4±0.1, 0.3±0.1 respectively, which were comparable to the MOD scores in Cluster 1 (P=0.34, 0.22, 0.28 respectively) over the same time frame. The early discharged patients (prior to day 5, average ICU LOS=2.0±0.1) also showed better outcomes (total LOS=5.0±0.5, P=0.002; days on mechanical ventilation=0.4±0.1, P=0.001) when compared to Cluster 1. The remaining five excluded patients had incomplete MOD score values despite ICU LOS longer than 5 days (14 to 43 days).

The characteristics of the non-survivor cohort was described previously (Abboud A, et al. Computational Analysis Supports an Early, Type 17 Cell-Associated Divergence of Blunt Trauma Survival and Mortality. *Crit Care Med* 2016: 44(11):e1 074-e1081), including MOD score patterns, complications, dynamic changes in inflammatory biomarker levels, and DyNA of systemic inflammation networks. Fifteen out of the 21 non-survivor patients survived to day 5, and these patients had average MOD score D2-5 of 3.6±0.7. To provide a comparison of the average MOD score values over time among the four clusters identified for survivors and the non-survivor cohort, we inserted the MOD score averages D2-5 from the published non-survivor cohort with the curves for the survivor cohort. Although confounded by the impact of patient drop-out in the non-survivor cohort, it is interesting to note that MOD score values start on average lower in non-surviving patients than surviving patients in Clusters 3 and 4 but then rise steadily. Thus, patients at risk for dying in-hospital beyond the first 24 h may exhibit unique MOD score patterns compared to patients that survive to discharge.

In the current example, we set out to identify organ dysfunction phenotypes in severely injured trauma patients that survive to discharge using an unsupervised clustering strategy. The FCM followed by CVIs defined four distinct MODS patterns. These four clusters were not only different in the magnitude of MODS, but also in organ failure patterns exhibited by unique patterns of six Marshall MODS components. The clusters also differed both in the clinical features and inflammatory profiles upon admission and over time up to day 5 post-injury. This analysis suggests that it may be feasible to stratify critically ill trauma patients early in the clinical course into sub-groups at risk for multiple clinical trajectories defined by specific patterns and magnitude of organ dysfunction.

The following numbered clauses provide illustrative aspects of the present invention.

1. A method of managing a trauma injury patient or a method of determining risk of multiple organ dysfunction in a patient, comprising:
   obtaining within a window of time after injury a patient's values for members of a panel of biomarkers, clinical variables, and/or genetic polymorphisms that are, as a group, able to segregate, using one or more statistical and/or mathematical methods on a data set of a statistically-significant size, patients at least into group of patients that experience high risk, and patients that experience low risk, of multiple organ dysfunction with clinically-acceptable specificity and selectivity;
   determining, using a computer-implemented method, a value for the obtained patient's values for each member of the panel of biomarkers, clinical variables, and/or genetic polymorphisms against a set of stored values for a statistically-significant number of patients, and calculating a representation of those values to produce a panel value;

determining, using a computer-implemented method, if the panel value for the patient is within a range of panel values for the set of stored values within which patients experience a clinically-relevant risk of multiple organ dysfunction or nosocomial infection; and producing, using a computer-implemented method, an output indicating whether the patient is expected to experience a risk of multiple organ dysfunction or nosocomial infection.

2. The method of clause 1, wherein the range of panel values is a range or cluster of values, representing a different predicted patient outcome.

3. The method of clause 1, comprising:

obtaining a patient's values for members of a panel of biomarkers, clinical variables, and/or genetic polymorphisms that are, as a group, able to segregate, using a statistical ranking method on a data set of a statistically-significant size, patients into a group of patients that experience multiple organ dysfunction with clinically-acceptable specificity and selectivity (that is, specificity and selectivity that a clinician would consider sufficiently clinically relevant for decision-making purposes);

determining, using a computer-implemented method, a rank value for the obtained patient's values for each member of the panel of biomarkers, clinical variables, and/or genetic polymorphisms against a set of stored values for a statistically-significant number of patients, and calculating a representation of those rank values of those rank values to produce a panel rank value;

determining, using a computer-implemented method, if the panel rank value for the patient is above or below a panel rank value threshold for the set of stored values above which patients experience a clinically-relevant risk of multiple organ dysfunction or nosocomial infection; and producing, using a computer-implemented method, an output indicating whether the patient is expected to experience a clinically-relevant, significant risk of multiple organ dysfunction or nosocomial infection.

4. The method of clause 3, wherein the panel rank value is a rank sum value for members, such as all members of the panel other than those generating binary values.

5. The method of clause 4, wherein the panel rank threshold is a panel rank sum value above which patients experience a clinically-relevant risk of multiple organ dysfunction or nosocomial infection that is at least 55%, 56%, 57%, 58%, 59%, 60%, 61%, 62%, 63%, 64%, or 65% of the maximum panel rank sum value for the stored values.

6. The method of clause 4, wherein the panel rank threshold is a panel rank sum value above which patients experience a clinically-relevant risk of multiple organ dysfunction or nosocomial infection that is at least 61% of the maximum panel rank sum value for the stored values.

7. The method of any one of clauses 1-6, wherein the patient's values for members of a panel of biomarkers and clinical variables are obtained within a window of time (time frame) of from immediately after injury to one month after injury, such as ranging from one minute, five minutes, ten minutes, 15 minutes, 30 minutes, 1 hour, or two hours after injury to one hour, two hours, three hours, four hours, five hours, six hours, seven hours, eight hours, nine hours, 10 hours, 12 hours, 18 hours, 24 hours, 36 hours, 48 hours, one week, or two weeks after injury, including increments therebetween, such as from 1 minute to 48 hours after injury, from 5 minutes to 36 hours after injury, or from 10 minutes to 24 hours after injury.

8. The method of any one of clauses 1-7, wherein the patient is admitted to an intensive care unit and has a likelihood of survival of at least 24 hours.

9. The method of any one of clauses 1-8, wherein the trauma is blunt trauma, such as non-penetrating blunt trauma.

10. The method of any one of clauses 1-9, wherein the statistical and/or mathematical method segregates patients into a group of patients that experience multiple organ dysfunction an average multiple organ dysfunction score as measured on days 2-5 after injury.

11. The method of clause 10, wherein the multiple organ dysfunction score is an average Marshall's multiple organ dysfunction score as measured on days 2, 3, 4, and 5 after injury (a$MOD_{D2-D5}$), where a score of less than or equal to three is indicative of no multiple organ dysfunction, and a score of greater than three is indicative of multiple organ dysfunction.

12. The method of any one of clauses 1-11, further comprising adding the patient's values and the patient's outcome, including a$MOD_{D2-D5}$, or an equivalent thereof, survival, and/or presence of nosocomial infection, to the set of stored values.

13. The method of any one of clauses 1-12, wherein the stored data set comprises at least 100, 200, 300, 376, or 400 values from different patients for each member of the panel of biomarkers, clinical variables, and/or genetic polymorphisms.

14. The method of any one of clauses 1-13, wherein the panel of biomarkers, clinical variables, and/or genetic polymorphisms includes one or more polymorphism selected from:

homozygous (AA) for a cytosine (C) at rs10741668, or a polymorphism in linkage disequilibrium therewith, such as where $D'>0.75$ or $R^2>0.75$;

homozygous for a guanine (G) at rs10790334, or a polymorphism in linkage disequilibrium therewith, such as where $D'>0.75$ or $R^2>0.75$;

homozygous for a C at rs2065418, or a polymorphism in linkage disequilibrium therewith, such as where $D'>0.75$ or $R^2>0.75$;

heterozygous (AB) for a G at rs2241777, or a polymorphism in linkage disequilibrium therewith, such as where $D'>0.75$ or $R^2>0.75$;

heterozygous for a thymine (T) at rs3134287, or a polymorphism in linkage disequilibrium therewith, such as where $D'>0.75$ or $R^2>0.75$;

heterozygous for an adenine (A) at rs3098223, or a polymorphism in linkage disequilibrium therewith, such as where $D'>0.75$ or $R^2>0.75$; and heterozygous for a T at rs906790, or a polymorphism in linkage disequilibrium therewith, such as where $D'>0.75$ or $R^2>0.75$.

15. The method of any one of clauses 1-14, wherein the panel of biomarkers, clinical variables, and/or genetic polymorphisms includes one or more polymorphism selected from:

homozygous (AA) for a cytosine (C) at rs10741668;
homozygous for a guanine (G) at rs10790334f;
homozygous for a C at rs2065418;
heterozygous (AB) for a G at rs2241777;

heterozygous for a thymine (T) at rs3134287; heterozygous for an adenine (A) at rs3098223; and heterozygous for a T at rs906790.

16. The method of any one of clauses 1-15, wherein the panel of biomarkers, clinical variables, and/or genetic polymorphisms includes the genetic polymorphism of homozygous for a C at rs2065418.
17. The method of any one of clauses 1-16, wherein the panel of biomarkers, clinical variables, and/or genetic polymorphisms comprise: interleukin 10 (IL-10), MCP-1/CCL2, Cl, $CO_2$, creatinine, partial thromboplastin time (PTT), and platelet counts.
18. The method of any one of clauses 1-17, wherein the panel of biomarkers, clinical variables, and/or genetic polymorphisms consists of: interleukin 10 (IL-10), MCP-1/CCL2, Cl, $CO_2$, creatinine, partial thromboplastin time (PTT), and platelet counts.
19. The method of any one of clauses 1-18, wherein the panel of biomarkers, clinical variables, and/or genetic polymorphisms comprise one or more, or all of: IL-6, MCP-1, IL-10, IL-8, IP-10, sST2, and MIG.
20. The method of any one of clause 3-19, wherein the panel rank threshold above which patients experience a clinically-relevant risk of multiple organ dysfunction or nosocomial infection is at least 55%, 56%, 57%, 58%, 59%, 60%, 61%, 62%, 63%, 64%, or 65% of the maximum panel rank.
21. The method of any one of clauses 1-20, further comprising performing the method on one or more additional patients and categorizing the patients in at least two groups, including: a first group of patients is expected not to experience a significant risk of multiple organ dysfunction or nosocomial infection, and a second group of patients expected to experience a significant risk of multiple organ dysfunction or nosocomial infection.
22. The method of clause 21, further comprising treating the patients with a compound or composition, such as an anti-inflammatory compound, that is being evaluated for safety and effectiveness in prevention or treatment of multiple organ dysfunction syndrome.
23. The method of any one of clauses 1-22, further comprising when a patient is indicated in the output to be expected to experience a significant risk of multiple organ dysfunction or nosocomial infection, treating the patient with an effective amount of a therapeutic agent effective for treatment of multiple organ dysfunction syndrome, that is optionally an immune modulator or an anti-inflammatory therapeutic agent, such as a compound or composition for use in decreasing a Th17 inflammatory response, and/or an antibiotic.
24. A system comprising a computer, instructions for performing the method of any one of clauses 1-21, and a computer-readable medium comprising the set of stored values for a statistically-significant number of patients for panel of patient biomarkers, clinical variables, and/or genetic polymorphisms.

Although the invention has been described in detail for the purpose of illustration based on what is currently considered to be the most practical aspects, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A computer-implemented method of determining risk of developing multiple organ dysfunction (MOD) in a trauma patient, comprising:
generating, with a processor, a dataset of stored values comprising an $aMOD_{D2-D5}$ value for a statistically-significant number of patients and a diagnosis of a nosocomial infection, the $aMOD_{D2-D5}$ value comprising a MOD score, obtained on days 2-5 following a trauma injury based on a machine learning model trained with a regression analysis, the regression analysis applied to a panel of biomarkers, the panel of biomarkers comprising one or more of interleukin 6, interleukin 8/CCL8, interleukin 10, IFN-γ inducible protein (IP)-10, plasma levels of soluble ST2, monokine induced by gamma interferon, monocyte chemotactic protein (MCP)-1, chloride, $CO_2$, creatinine, partial thromboplastin time (PTT), and platelet count, and one or more polymorphisms selected from:
homozygous (AA) for a cytosine (C) at rs10741668, or a polymorphism in linkage disequilibrium therewith, where $D'>0.75$ or $R^2>0.75$;
homozygous for a guanine (G) at rs10790334, or a polymorphism in linkage disequilibrium therewith, where $D'>0.75$ or $R^2>0.75$;
homozygous for a C at rs2065418, or a polymorphism in linkage disequilibrium therewith, where $D'>0.75$ or $R^2>0.75$;
heterozygous (AB) for a G at rs2241777, or a polymorphism in linkage disequilibrium therewith, where $D'>0.75$ or $R^2>0.75$;
heterozygous for a thymine (T) at rs3134287, or a polymorphism in linkage disequilibrium therewith, where $D'>0.75$ or $R^2>0.75$;
heterozygous for an adenine (A) at rs3098223, or a polymorphism in linkage disequilibrium therewith, where $D'>0.75$ or $R^2>0.75$; and
heterozygous for a T at rs906790, or a polymorphism in linkage disequilibrium therewith, where $D'>0.75$ or $R^2>0.75$;
calculating, with a processor and based on the dataset of stored values, a threshold $aMOD_{D2-D5}$ value indicative of a risk of developing MOD;
generating, with the machine learning model, a MOD score for days 2-5 following a trauma injury experienced by a trauma patient;
calculating, with a processor and based on the MOD scores generated by the machine learning model, an $aMOD_{D2-D5}$ value for the trauma patient;
determining, with a processor and based on the threshold, whether the trauma patient's $aMOD_{D2-D5}$ value meets the calculated threshold and thus whether the trauma patient has a clinically-relevant risk of developing MOD; and
generating, with a processor, an output indicating whether the patient is expected to experience a risk of MOD.

2. The method of claim 1, wherein the threshold is calculated using a decision list analysis.

3. The method of claim 2, wherein the threshold $aMOD_{D2-D5}$ value is 3.

4. The method of claim 3, wherein an $aMOD_{D2-D5}$ value of less than or equal to 3 is indicative of a low risk of developing MOD, and an $aMOD_{D2-D5}$ value of greater than 3 is indicative of a high risk of developing MOD.

5. The method of claim 1, wherein the panel of biomarkers comprises MCP-1, interleukin 10, chloride, $CO_2$, creatinine, platelets count, and PTT.

6. The method of claim 1, wherein the panel of biomarkers comprises interleukin 6, MCP-1/CCL2, interleukin 10, and interleukin 8/CCL8.

7. The method of claim 1, wherein the panel of biomarkers comprises interleukin 10, MCP-1/CCL2, chloride, $CO_2$, creatinine, PTT, and platelet count.

8. The method of claim 1, further comprising updating the dataset with the trauma patient's $aMOD_{D2-D5}$ value and diagnosis.

9. A system for determining risk of developing multiple organ dysfunction (MOD) in a trauma patient, the system comprising a processor programmed or configured to:
   generate a dataset of stored values comprising an $aMOD_{D2-D5}$ value for a statistically-significant number of patients and a diagnosis of a nosocomial infection, the $aMOD_{D2-D5}$ value comprising a MOD score, obtained on days 2-5 following a trauma injury based on a machine learning model that was trained with a regression analysis, the regression analysis applied to a panel of biomarkers, the panel of biomarkers comprising one or more of interleukin 6, interleukin 8/CCL8, interleukin 10, IFN-γ inducible protein (IP)-10, plasma levels of soluble ST2, monokine induced by gamma interferon, monocyte chemotactic protein (MCP)-1, chloride, $CO_2$, creatinine, partial thromboplastin time (PTT), and platelet count, and one or more polymorphisms selected from:
      homozygous (AA) for a cytosine (C) at rs10741668, or a polymorphism in linkage disequilibrium therewith, where D'>0.75 or $R^2$>0.75;
      homozygous for a guanine (G) at rs10790334, or a polymorphism in linkage disequilibrium therewith, where D'>0.75 or $R^2$>0.75;
      homozygous for a C at rs2065418, or a polymorphism in linkage disequilibrium therewith, where D'>0.75 or $R^2$>0.75;
      heterozygous (AB) for a G at rs2241777, or a polymorphism in linkage disequilibrium therewith, where D'>0.75 or $R^2$>0.75;
      heterozygous for a thymine (T) at rs3134287, or a polymorphism in linkage disequilibrium therewith, where D'>0.75 or $R^2$>0.75;
      heterozygous for an adenine (A) at rs3098223, or a polymorphism in linkage disequilibrium therewith, where D'>0.75 or $R^2$>0.75; and
      heterozygous for a T at rs906790, or a polymorphism in linkage disequilibrium therewith, where D'>0.75 or $R^2$>0.75;
   calculate, based on the dataset of stored values, a threshold $aMOD_{D2-D5}$ value indicative of a risk of developing MOD;
   generate, with the machine learning model, MOD scores for days 2-5 following a trauma injury experienced by a trauma patient;
   calculate, with a processor and based on the MOD scores generated by the machine learning model, an $aMOD_{D2-D5}$ value for the trauma patient;
   determine, based on the threshold, whether the trauma patient's $aMOD_{D2-D5}$ value meets the calculated threshold and thus whether the trauma patient has a clinically relevant risk of developing MOD; and
   generate an output indicating whether the patient is expected to experience a risk of MOD.

10. The system of claim 9, wherein the processor is further programmed or configured to calculate the threshold using a decision list analysis.

11. The system of claim 10, wherein the threshold $aMOD_{D2-D5}$ value is 3.

12. The system of claim 11, wherein the processor is further programmed or configured to classify an $aMOD_{D2-D5}$ value of less than or equal to 3 as being indicative of a low risk of developing MOD, and to classify an $aMOD_{D2-D5}$ value of greater than 3 as being indicative of a high risk of developing MOD.

13. The system of claim 9, wherein the panel of biomarkers comprises MCP-1, interleukin 10, chloride, $CO_2$, creatinine, platelets count, and PTT.

14. The system of claim 9, wherein the panel of biomarkers comprises interleukin 6, MCP-1/CCL2, interleukin 10, and interleukin 8/CCL8.

15. The system of claim 9, wherein the panel of biomarkers comprises interleukin 10, MCP-1/CCL2, chloride, $CO_2$, creatinine, PTT, and platelet count.

16. The system of claim 9, wherein the processor is further programmed or configured to update the dataset with the trauma patient's $aMOD_{D2-D5}$ value and diagnosis.

17. A computer-implement method of determining risk of developing multiple organ dysfunction (MOD) in a trauma patient, comprising:
   training, with a processor and using a machine learning model, a model for determining risk of developing MOD, the training based on a dataset of stored values generated from a regression analysis applied to a panel of biomarkers, the panel of biomarkers comprising one or more of interleukin 6, interleukin 8/CCL8, interleukin 10, IFN-γ inducible protein (IP)-10, plasma levels of soluble ST2, monokine induced by gamma interferon, monocyte chemotactic protein (MCP)-1, chloride, $CO_2$, creatinine, partial thromboplastin time (PTT), and platelet count, and one or more polymorphisms selected from:
      homozygous (AA) for a cytosine (C) at rs10741668, or a polymorphism in linkage disequilibrium therewith, where D'>0.75 or $R^2$>0.75;
      homozygous for a guanine (G) at rs10790334, or a polymorphism in linkage disequilibrium therewith, where D'>0.75 or $R^2$>0.75;
      homozygous for a C at rs2065418, or a polymorphism in linkage disequilibrium therewith, where D'>0.75 or $R^2$>0.75;
      heterozygous (AB) for a G at rs2241777, or a polymorphism in linkage disequilibrium therewith, where D'>0.75 or $R^2$>0.75;
      heterozygous for a thymine (T) at rs3134287, or a polymorphism in linkage disequilibrium therewith, where D'>0.75 or $R^2$>0.75;
      heterozygous for an adenine (A) at rs3098223, or a polymorphism in linkage disequilibrium therewith, where D'>0.75 or $R^2$>0.75; and
      heterozygous for a T at rs906790, or a polymorphism in linkage disequilibrium therewith, where D'>0.75 or $R^2$>0.75;
   calculating, with a processor and based on the dataset of stored values, a threshold $aMOD_{D2-D5}$ value indicative of a risk of developing MOD;
   applying, with a processor, the model to a first set of the biomarkers for a trauma patient to obtain MOD scores for days 2-5 following a trauma injury experienced by the trauma patient; and
   generating, with a processor and based on the threshold and the MOD scores for days 2-5 for the trauma patient, an output indicating whether the trauma patient is expected to experience a risk of MOD.

18. The method of claim 17, wherein the panel of biomarkers comprises MCP-1, interleukin 10, chloride, $CO_2$, creatinine, platelets count, and PTT.

19. The method of claim 17, wherein the panel of biomarkers comprises interleukin 6, MCP-1/CCL2, interleukin 10, and interleukin 8/CCL8.

20. The method of claim 17, wherein the panel of biomarkers comprises interleukin 10, MCP-1/CCL2, chloride, $CO_2$, creatinine, PTT, and platelet count.

* * * * *